(12) United States Patent
Balogh et al.

(10) Patent No.: US 11,617,356 B2
(45) Date of Patent: Apr. 4, 2023

(54) MOUSE LYMPHOMA CELL LINE AND ANIMAL MODEL OF HUMAN HIGH GRADE B-CELL LYMPHOMA

(71) Applicant: PÉCSI TUDOMÁNYEGYETEM, Pécs (HU)

(72) Inventors: Péter Balogh, Pécs (HU); Dávid Ernszt, Komló (HU); Tamás Kovács, Pécs (HU)

(73) Assignee: Pécsi Tudományegyetem, Pécs (HU)

( * ) Notice: Subject to any disclaimer, the term of this patent is extended or adjusted under 35 U.S.C. 154(b) by 1347 days.

(21) Appl. No.: 15/770,811

(22) PCT Filed: Oct. 26, 2016

(86) PCT No.: PCT/HU2016/050052
§ 371 (c)(1),
(2) Date: Apr. 25, 2018

(87) PCT Pub. No.: WO2017/072544
PCT Pub. Date: May 4, 2017

(65) Prior Publication Data
US 2018/0255752 A1    Sep. 13, 2018

(30) Foreign Application Priority Data
Oct. 26, 2015   (HU) .................................. P1500507

(51) Int. Cl.
*A01K 67/027*   (2006.01)
*C12N 5/09*     (2010.01)

(52) U.S. Cl.
CPC ........ *A01K 67/0271* (2013.01); *C12N 5/0694* (2013.01); *A01K 2207/12* (2013.01); *A01K 2227/105* (2013.01); *A01K 2267/0331* (2013.01); *A01K 2267/0381* (2013.01)

(58) Field of Classification Search
CPC ............ A01K 67/0271; A01K 2207/12; A01K 2227/105; A01K 2267/0331; A01K 2267/0381; C12N 5/0694; C12N 5/06
See application file for complete search history.

(56) References Cited

U.S. PATENT DOCUMENTS 5,849,990 A     12/1998  Hochman
2008/0070256 A1  3/2008  Refaeli et al.

OTHER PUBLICATIONS

Bell et al. "Antigen-capturing Cells Can Masquerade as Memory B Cells." J Exp Med. May 19, 2003; 197(10): 1233-1244. (Year: 2003).*
Castillo-Mendez et al. "Characterization of the spleen B-cell compartment at the early and late blood-stage *Plasmodium chabaudi* malaria." Scand J Immunol .Aug.-Sep. 2007;66(2-3):309-19. (Year: 2007).*
Wadermann et al. "B-1a B Cells that Link the Innate and Adaptive Immune Responses Are Lacking in the Absence of the Spleen." J Exp Med. Mar. 18, 2002; 195(6): 771-780. (Year: 2002).*
Slavin et al. "Spontaneous murine B-cell leukaemia." Nature vol. 272, pp. 624-626 (1978). (Year: 1978).*
Hagan, C. "When Mice are considered old?" The Jackson Laboratory. retrivied from https://www.jax.org/news-and-insights/jax-blog/2017/november/when-are-mice-considered-old on Jan. 25, 2022. (Year: 2022).*
Triplett et al. "Abstract A02: Altered myeloid cells in the tumor microenvironment promote growth of T cell acute lymphoblastic leukemia." Clin Cancer Res Sep. 2015;21 (17 Suppl):Abstract nr A02. (Year: 2015).*
Donnou et al., "Murine Models of B-Cell Lymphomas: Promising Tools for Designing Cancer Therapies", Advances in Hematology, 2012, Article ID 701704, doi:10.1155/2012/701704, pp. 1-13.
Muppidi et al., "Loss of signalling via Gα13 in germinal centre B-cell-derived lymphoma", Nature, 2015, 516 (7530): 254-258, pp. 1-25.
Vojkovics et al., "Isolation and Characterization of a Murine Spontaneous High-Grade Follicular Lymphoma with Restricted In Vivo Spreading—a Model for Lymphatic Metastasis Via the Mesentery", Pathology Oncology Research, 2015, vol. 22, No. 2, pp. 421-430.
Teitell et al., "Lymphoid Malignancies", Mouse Models of Human Cancer, 2004, ISBN 0-471-44460, pp. 237-259.
Bseiso et al., "The Indolent Lymphomas", Cancer Network, Oncolocy Journal, 2005, Survivorship, pp. 1-35.
Bultema et al., "Epstein-Barr Virus LMP2A Accelerates MYC-Induced Lymphomagenesis"; Oncogene, 2009, 28 (11): 1471-1476, pp. 1-11.

* cited by examiner

Primary Examiner — Titilayo Moloye
(74) Attorney, Agent, or Firm — Jason D. Voight

(57) ABSTRACT

The invention relates to a new, spontaneous mouse lymphoma cell line displaying CD19, B220, MHC II, surface IgG2a/kappa chain and MAC-1, which is negative for CD5, animal models of B-cell lymphoma based on said cell line and methods for assessing lymphoma propagation and lymphoma expansion based on said cell line.

24 Claims, 16 Drawing Sheets

Figure 2:
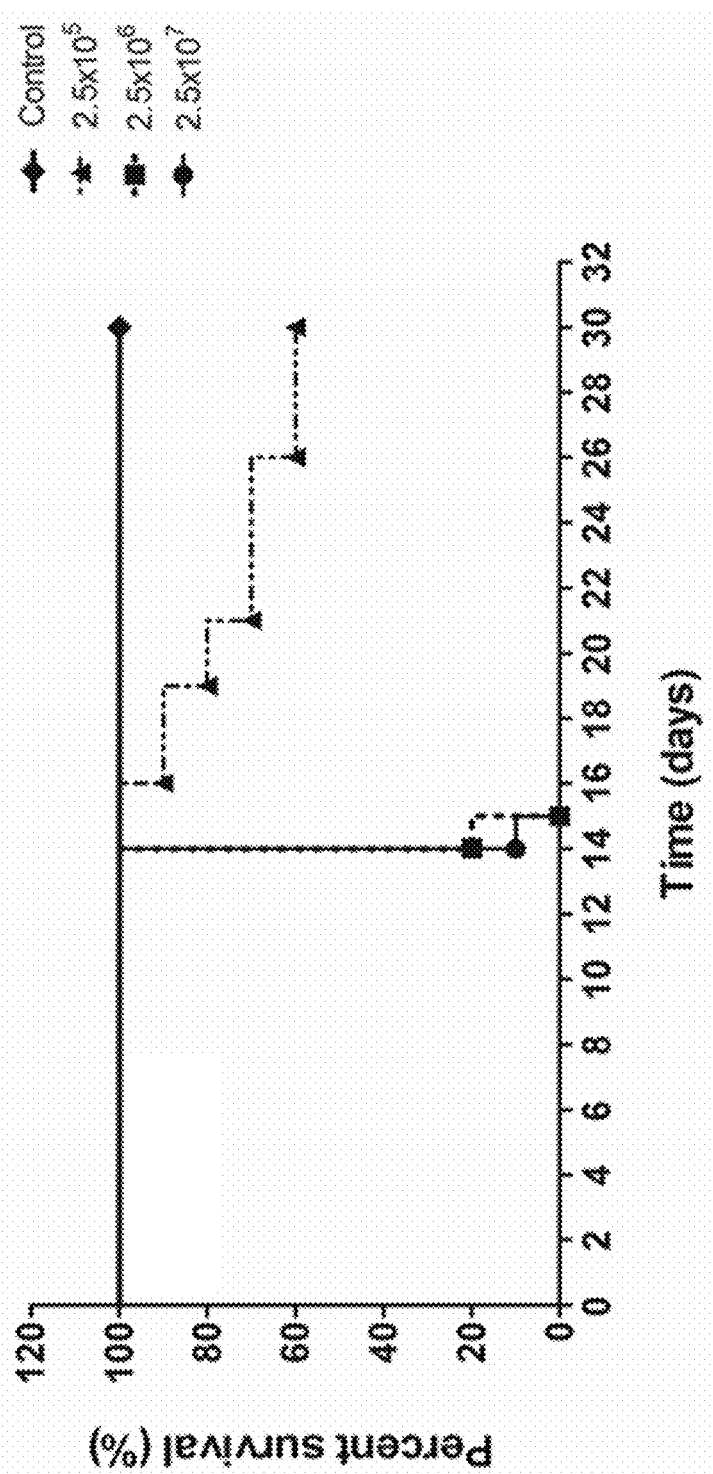

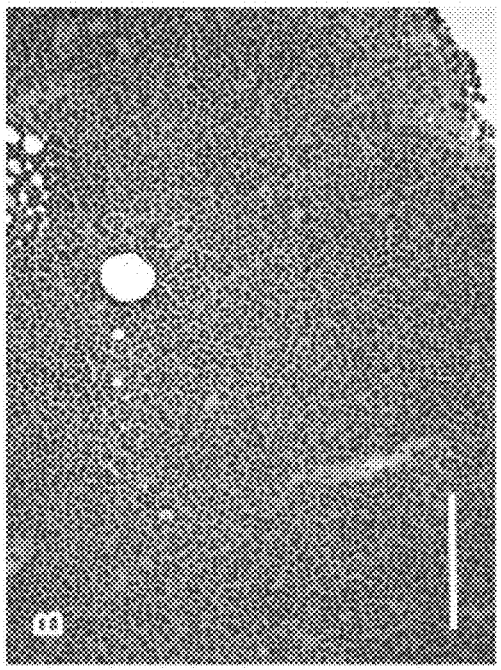
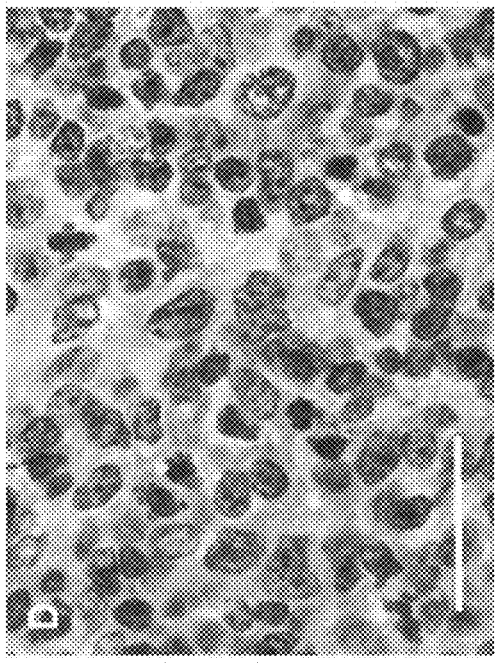
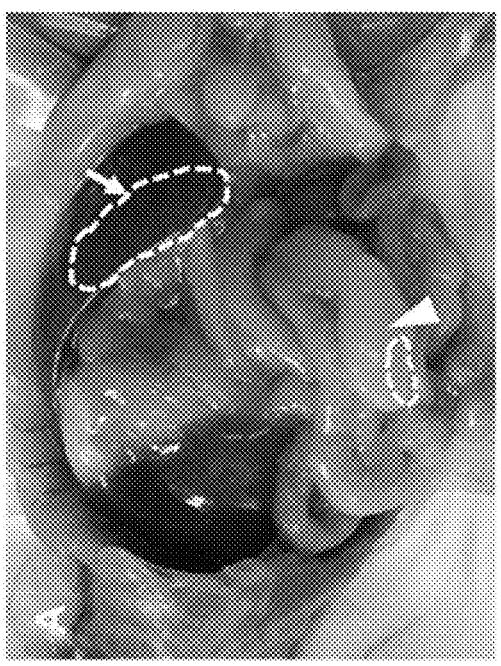
FIGURE 1

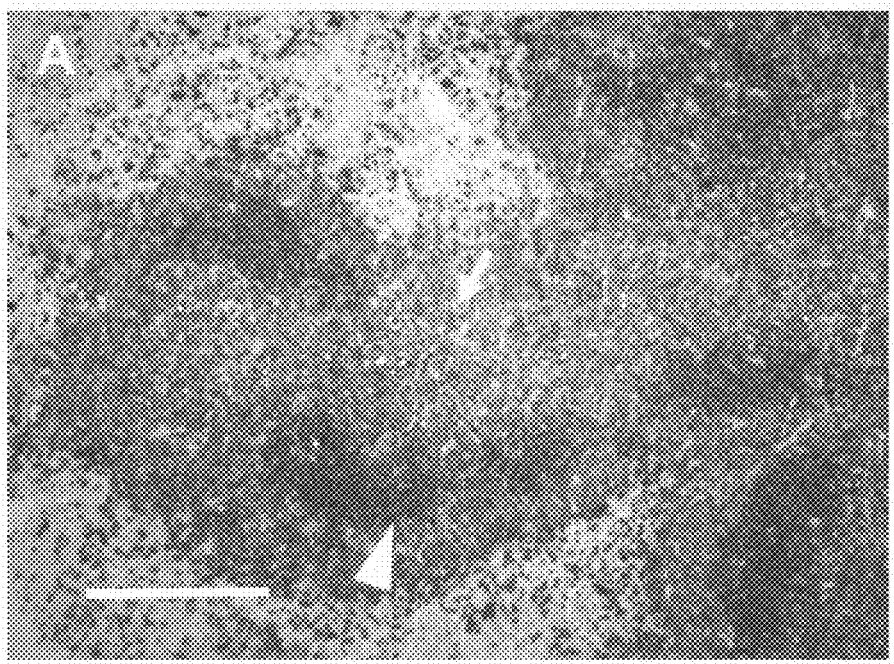
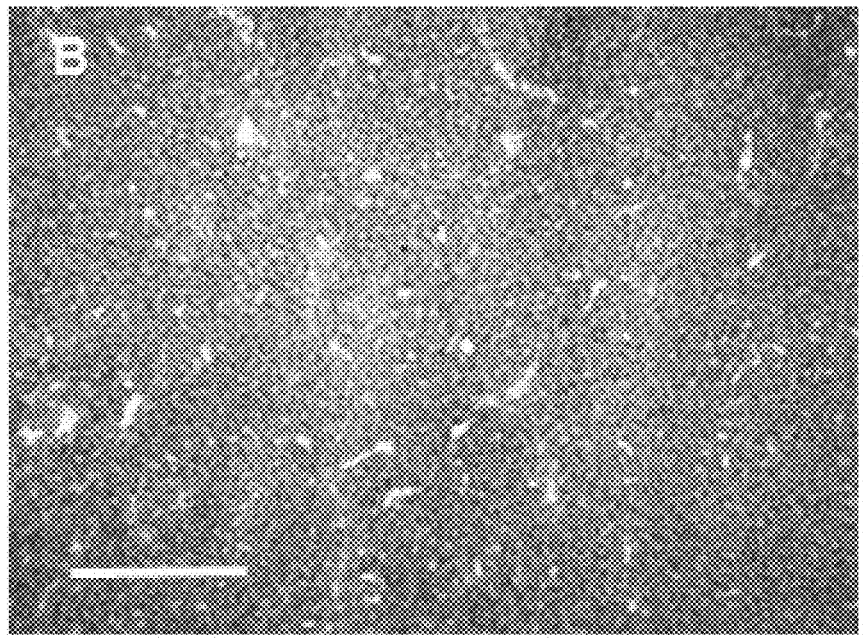
FIGURE 3A-B

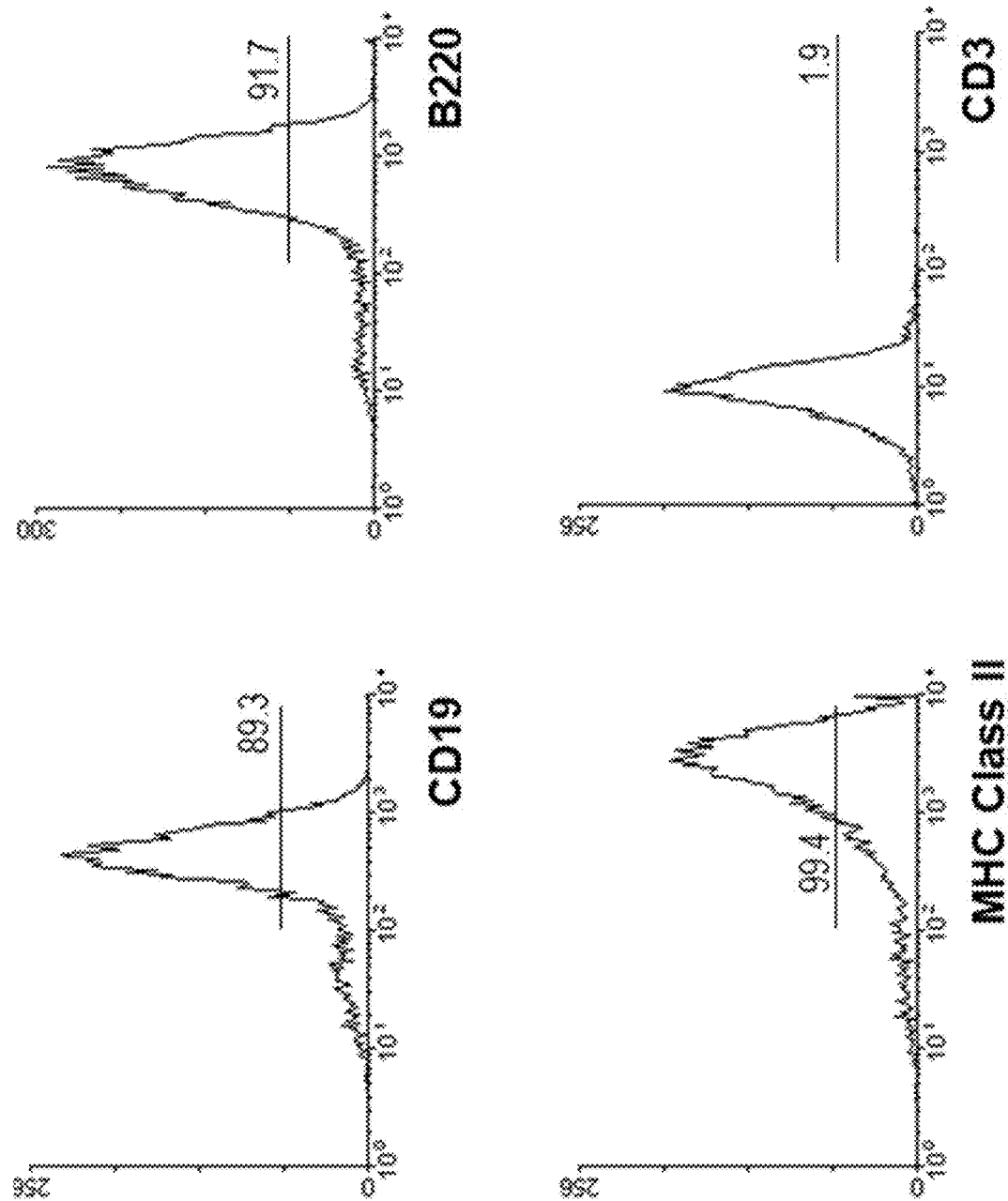
FIGURE 3C/1

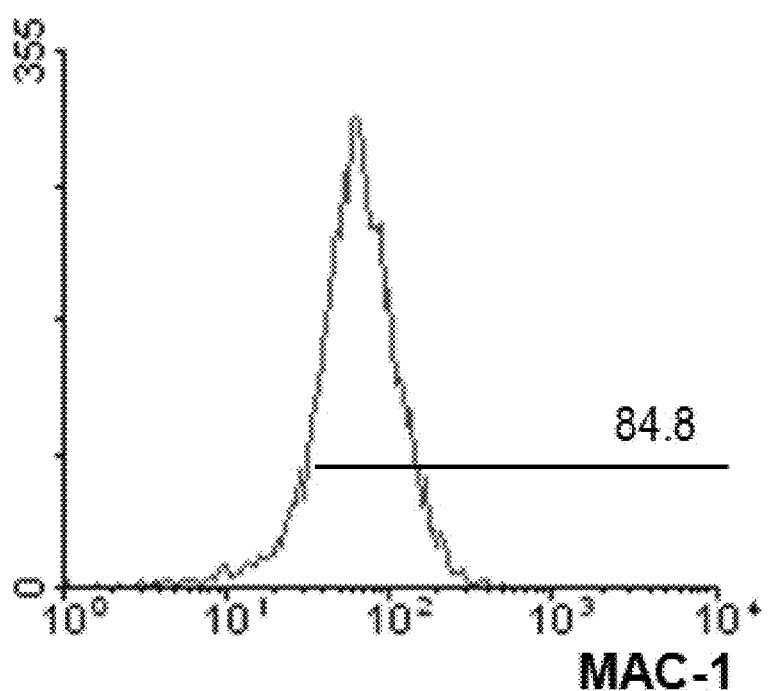
FIGURE 3C/2

XenoLight DiR (24h)

Omentum

CFSE/HRP a-FITC

MOUSE LYMPHOMA CELL LINE AND ANIMAL MODEL OF HUMAN HIGH GRADE B-CELL LYMPHOMA

This is the national stage of International Application PCT/HU2016/050052, filed Oct. 26, 2016.

FIELD OF THE INVENTION

The invention relates to a new, spontaneous mouse lymphoma cell line displaying CD19, B220, MHC II, surface IgG2a/kappa chain and MAC-1, which is negative for CD5, animal models of high grade B-cell lymphoma based on said cell line and methods for assessing lymphoma propagation and expansion based on said cell line.

BACKGROUND OF THE INVENTION

Maturation of resting B lymphocytes following antigen stimulation into plasma cells or memory B cells in peripheral lymphoid tissues is a multistep process requiring a tightly regulated sequence of activation, proliferation and clonal selection. In this process uncontrolled expression of a limited number of crucial genes leads to various forms of differentiation blockade, causing abnormal proliferation or survival of transformed B cells. Depending on the phenotypic and genotypic traits, the resulting B-cell malignancies have broadly variable differentiation stages of affected cells, cellular composition and lymphoid and other tissue involvement [1, 2].

For the more efficient diagnosis and therapy of human B-cell lymphomas, various B-cell tumors in mice have proved invaluable tools. For a review on spontaneous and induced lymphomas in wide type or genetically engineered mice see e.g. [18]. For a classification of lymphoid neoplasms in mice, see [19]. Earlier these tumors arose either spontaneously or were induced by ionizing irradiation, exposure to chemical agents or viral transformation [3]. Subsequent identification of certain key elements (such as c-myc and Bcl-2) involved in the malignant transformation of B cells in humans combined with the ability to manipulate the mouse genome has greatly expanded the potential research models [4, 5], but also raised the importance of species differences, as various murine models were often found to be different from the parallel human conditions, including both the phenotypic characteristics of malignant cells and the course of the disease [5, 6]. This divergence may reflect important structural differences between the human and mouse lymphoid organs themselves (such as the composition of splenic marginal zone and Peyer's patches, [7]) or the divergent expression pattern of cell surface markers used for the identification of various B-cell subsets 9. The most widely used transgenic mouse model is Eµ-Myc. In this transgenic experimental tumor model the myc gene is inserted into the IgH locus and B-cell lymphomas develop at a 100% incidence rate. Nonetheless, disease onset is highly variable, as is the phenotype of the tumors in different mice [21].

Immunodeficient or immunocompromised host animals are often used as host of modified or spontaneous tumor cells. While such models promote our understanding the mechanisms linked to lymphomagenesis in more detail, they also possess significant drawbacks like the lesser degree of resemblance to the human situation and the cost of specific animals and rearing conditions.

Human diffuse large B-cell lymphoma (DLBCL) represents the most common subtype of non-Hodgkin lymphoma worldwide. Although DLBCL is typically aggressive and results in a disease that is fatal without treatment, it is readily curable with immunochemotherapy in the majority of patients. However, a minority of patients are left uncured even in the rituximab era. The current (2016) version of the World Health Organization (WHO) classification of lymphoid malignancies acknowledges the heterogeneity of DLBCL (not otherwise specified), as well as a variety of DLBCLsubtypes. Among these subtypes is activated B cell (ABC) DLBCL, according to Bcl-2/Bcl-6 and c-myc expression criteria, which accounts to approximately 15-20% of all DLBCL cases in humans [22].

In addition to providing potential in vivo models for human diseases, murine B cell lymphomas may also offer experimental opportunities to study the mechanisms of interactions between the lymphoid and non-hematopoietic constituents in peripheral lymphoid tissues. These include the preserved capacity of lymphoma cells to selectively colonize peripheral lymphoid tissues via organ-selective homing and subsequent positioning within suitable microenvironmental niches, as an analogue to the lymphocyte compartmentalization under physiological conditions, including their capacity to modulate their stromal milieu [8, 9] and to be modulated by the same. To study the above mechanisms, a well-established and detectable cell marker pattern is desirable.

Several lymphoma cell lines are available for research. U.S. Pat. No. 5,849,990 for example describes a lymphoma causing cell line capable of infiltrating into the CNS or eye of the inoculated host BALB/c mice. The Rev-2-T-6 cells of U.S. Pat. No. 5,849,990 are of T-cell origin. BCL-1, the first-reported case of a spontaneously developed mouse B-lymphoma, expresses CD5, surface IgM, Mac-1, CD43 and low level of B220, and is considered to be a typical B-1 cell-derived lymphoma [25]. The 38C13 Her2/neu cell line is a genetically engineered variant of the highly malignant murine B cell lymphoma 38C13.

Although spontaneous and induced lymphoma cell lines and models are described in the art, the etiology, progression and classification of these pathogenies are still not fully understood. A more thorough understanding is needed of the mechanisms by which the forms of lymphomas are initiated, progress and influenced by their environment. Besides a better understanding of tumor cell migration (tumor expansion), results obtained from lymphoma research may further our knowledge of normal B-cell distribution and behavior. Another issue of interest may be the interaction of tumor stroma and cancer cells.

SHORT DESCRIPTION OF THE INVENTION

The invention provides cells suitable for the assessment of B-cell lymphoma migration. The specific migration and distribution profile of the lymphoma offers a good opportunity to determine homing sites, homing markers, addressins, etc. of lymphoma migration and to find differences to normal B-cell migration and distribution. Further, the cells according to the invention are a suitable laboratory tool to assess the effects of tumor microenvironment (i.e. tumor stroma) on the propagation of B-cell lymphomas.

1. The invention relates to cells of the mouse lymphoma cell line deposited at the Deutsche Sammlung von Mikroorganismen und Zellkulturen (Leibniz-Institut DSMZ-Deutsche Sammlung von Mikroorganismen und Zellkulturen GmbH; DSMZ; Inhoffenstraße 7B38124 Braunschweig GERMANY) on Sep. 24, 2015 under the number DSMZ ACC3278 or a population of cells derived thereof, wherein said derived cells are positive for CD19, B220, MHC II, surface IgG2a/kappa chain and MAC-1, negative for CD5. The cells preferably comprise a chromosomal translocation selected from t(10:6), t(6:10), t(11:19) and t(10:11).

2. In a preferred embodiment the cells co-express BAFF-R (B-cell activating factor receptor), BCMA (B-cell maturation antigen) and TACI (Transmembrane activator and CAML interactor). The cells may express ICAM-1 (CD54) and LFA-1 (CD11α/CD18) molecules at a higher level compared to L-selectin (CD62L) and α4 integrin. The cells preferably do not express IgM, IgD, other IgG classes or IgA. The cells are negative for CD3. Preferably, rearrangement of IgH genes within the $V_H7183$ region can be detected. Preferably, Bcl expression is low or preferably may not be detected by indirect immunohistochemistry using 4B2 anti-mouse Bcl6 and 15C anti-Bcl7A monoclonal antibodies. The cells may be positive for Bcl7A. The cells may be negative or weakly positive for CXCR5 as determined by (immunostaining and) flow cytometric analysis. "Weak" expression refers to the staining results when the fraction of positive cells exceeding background fluorescence is less than 20% of the total and at less than 40% of mean fluorescence intensity (MFI) compared to that of normal B cells.

3. In a highly preferred embodiment the cells are positive for CD19, B220, MHC II, surface IgG2a/kappa chain and MAC-1, negative for CD5 and the expression of Bcl6 is below the levels of expression in a normal (non-cancerous) centroblast, while the cells are negative or weakly positive for CXCR5.

In a preferred embodiment the invention relates to cells as defined in the claims and in paragraphs 1-3 hereinabove, wherein the primary site of expansion following intraperitoneal administration of the cells according to the invention to a mouse is the omentum and the fat associated lymphoid clusters (FALC) located along the blood vessels in the mesentery within 7 days, preferably within 5 days or 4 days, preferably within 3 days, days and highly preferably within approximately 24 hours of the administration. The term "primary site of expansion" refers to the site(s) of localization of the cells according to the invention where the cells migrate before they colonize the spleen or the peripheral lymph nodes. The primary site of expansion is/are the abdominal tissues/organs colonized within approximately 2 days from the time of intraperitoneal administration of cells in the range of from $10^4$ to $5\times10^6$ cells/recipient, preferably $10^6$ to $5\times10^6$ cells/recipient. Primary site refers to the lymphoid tissues containing above-background (as compared to uninjected controls) staining of cells with lymphoma characteristics (high FSC, low FSC corresponding to blasts, co-expression of MAC-1, CD19 and $B220^{hi}$) followed by rapid expansion within 2-4 days.

In a preferred embodiment the invention relates to cells defined in the claims and in paragraphs 1-3 hereinabove, wherein a tissue/organ selected from the peripheral lymph nodes, spleen, bone marrow, thymus and Peyer's patches is substantially free of lymphomas up to approximately 3 days, preferably up to 4 days or up to 5 days following intraperitoneal administration of the cells to a mouse, preferably wherein the peripheral lymph nodes are substantially free of lymphomas up to 24 hours or 2 days, preferably up to 3 days or up to 4 days, even more preferably up to 5 days following intraperitoneal administration of the cells to a mouse.

In a preferred embodiment the peripheral lymph nodes and preferably a tissue/organ selected from bone marrow, Peyer's patches, the lung, kidneys and brain is substantially free of lymphomas up to approximately 7 days following intraperitoneal administration of $10^6$ to $5\times10^6$ cells/recipient to a mouse.

In a highly preferred embodiment the lymphoma cells colonize the omentum and the fat associated lymphoid clusters (FALC) located along the blood vessels in the mesentery within 24 hours of administration of $10^4$ to $5\times10^6$ cells/recipient, preferably $10^6$ to $5\times10^6$ to a mouse, followed by the mesenteric lymph nodes and the spleen. In a preferred embodiment the cells may be detected in a low number (i.e. in a number not exceeding 0.1-1% of all nucleated cells) or may not be detected outside the omentum and FALC located along the blood vessels in the mesentery within 2 days, preferably 24 hours of administration.

In a preferred embodiment the lymphoma cells are absent from any of the following organs/tissues: bone marrow, Peyer's patches, thymus, brain, kidney, muscle and lung up to 5 days, preferably up to 8 days, preferably up to 12 days and highly preferably up to the death of the animal when administered to a mouse i.p. in a dose of $10^4$ to $5\times10^6$ cells/recipient, preferably $10^6$ to $5\times10^6$ cells/recipient. Detection of the presence of cells according to the invention may be performed immunostaining with labeled antibodies (B220, MAC-1, CD5, CD19) followed by flow cytometric evaluation of the tissues. Examples for the detection of the location of tumor cells is described in the "Examples" section hereunder.

In a highly preferred embodiment the lymphoma cells are localized in a tissue selected from omentum and FALC located along the blood vessels in the mesentery and substantially absent from a tissue/organ selected from mesenteric lymph nodes and spleen and are absent from a tissue/organ selected from bone marrow, Peyer's platches, brain, thymus, kidney, muscle and lung up to 2 days, preferably up to 4 days or 5 days following administration. In another highly preferred embodiment the lymphoma cells are localized in a tissue/organ selected from omentum and FALC located along the blood vessels in the mesentery, mesenteric lymph nodes and spleen and are substantially absent from the peripheral lymph nodes and are absent from a tissue/organ selected from bone marrow, Peyer's platches, brain, thymus, kidney, muscle and lung up to 7 days, preferably up to 12 days following administration.

In highly preferred embodiments the administration is in a dose of $10^6$ to $5\times10^6$ cells/recipient and the route of administration is intraperitoneal.

In a preferred embodiment the invention relates to cells defined in the claims and in paragraphs 1-3 hereinabove, wherein within 7 days, preferably 5 days, more preferably 2 days following intraperitoneal administration of $10^4$ to $5\times10^6$ cells/recipient, preferably $10^6$ to $5\times10^6$ cells/recipient to a mouse, the cells expand to abdominal lymphatic tissue showing adhesion to the lymphoma cells mediated by PNAd and MAdCAM (tissue wherein both PNAd and MAdCAM act as homing addressin for the lymphoma cells). In a preferred embodiment the cells may not detected or may be detected in a low number (i.e. in a number not exceeding 0.1-1% of all nucleated cells) in tissues showing adhesion mediated by other homing addressins than both PNAd and MAdCAM up to 2 days, preferably 4 days, more preferably 6 days following administration. In a preferred embodiment the number of lymphoma cells up to 2 days, preferably 5 days, more preferably 7 days following administration in tissues showing adhesion mediated by PNAd and MAdCAM is significantly higher than in tissues showing different adhesion.

The invention also relates to the use of the cells defined in the claims or in paragraphs 1 to 3 hereinabove, for the assessment of B-cell lymphoma (cell) migration. In a preferred embodiment the cells are used in an in vivo method, wherein the method comprises the following steps:
administering the cells to a mouse,
detecting the localization of the lymphoma cells in the mouse, which are positive for CD19, B220, MHC II, surface IgG2a/kappa chain and MAC-1 and negative for CD5.

The cells may be administered intraperitoneally in a dose of $10^4$ to $5\times10^6$ cells/recipient, preferably $10^6$ to $5\times10^6$. In a preferred embodiment the detection of said cells is performed up to 7, preferably up to 5 days, preferably up to 4 days, preferably up to 3 days or 2 days or 24 hours after the administration of said cells. In a preferred embodiment the detection of localization of the lymphoma cells comprises determination of homing sites for B-cell lymphomas in the abdomen or homing molecules for B-cell lymphomas.

The invention also relates to the use of the cells defined in the claims or in paragraphs 1-3 hereinabove for the assessment of tumor microenvironment-lymphoma interactions, comprising
providing cells defined in the claims or in paragraphs 1-3 hereinabove
culturing said cells in the presence and/or absence of tumor stroma
administering an agent of interest to said culture
evaluating the effect of said agent on the propagation of said cells in the presence and/or absence of tumor stroma.

Methods for propagating the cells defined in the claims or in paragraphs 1-3 hereinabove are also provided. The method may comprise
providing cells defined in the claims or in paragraphs 1-3 hereinabove,
optionally, providing tumor stroma,
culturing said cells and the optionally present stroma in a culture medium suitable for B-lineage cells,
optionally, injecting the cultured cells positive for CD19, B220, MHC II, surface IgG2a/kappa, and MAC-1, and negative for CD5 (or cells as defined in paragraphs 1-3 hereinabove) into a recipient mouse.

In a preferred embodiment the method comprises
providing cells defined in the claims or in paragraphs 1-3 hereinabove,
providing tumor stroma,
co-culturing said cells and the tumor stroma in a culture medium suitable for B-lineage cells and optionally, injecting the cultured cells positive for CD19, B220, MHC II, surface IgG2a/kappa, and MAC-1, and negative for CD5 (or cells as defined in paragraphs 1-3 hereinabove) into a recipient mouse.

The method may comprise
providing cells defined in the claims or in paragraphs 1-3 hereinabove,
injecting said cells into a recipient mouse,
providing cells positive for CD19, B220, MHC II, surface IgG2a/kappa, and MAC-1, and negative for CD5 and tumor stroma from the mouse,
co-culturing the cells positive for CD19, B220, MHC II, surface IgG2a/kappa, and MAC-1, and negative for CD5 and the tumor stroma in a culture medium suitable for B-lineage cells.

A dose of $10^4$ to $5\times10^7$ cells/recipient may be administered to a mouse in the propagating methods.

Also provided are methods for the assessment of B-cell lymphoma (cell) expansion in vivo, comprising
administering cells defined in the claims or in paragraphs 1-3 hereinabove to a mouse,
detecting the localization of lymphoma in said mouse by the detection of cells positive for CD19, MAC-1 MHC II, surface IgG2a/kappa chain and B220 and negative for CD5 or by the detection of cells defined in the claims or in paragraphs 1-3 hereinabove.

The cells may be administered intraperitoneally in a dose of $10^4$ to $5\times10^6$ cells/recipient, preferably $10^6$ to $5\times10^6$. In a preferred embodiment the detection of said cells is performed up to seven, preferably up to 5 days, preferably up to 4 days, preferably up to 3 days or 2 days or 24 hours after the administration of said cells.

An in vitro method for the assessment of (in vivo) B-cell lymphoma microenvironment and B-cell lymphoma interactions is also provided, the method comprising
providing cells defined in the claims or in paragraphs 1-3 hereinabove
culturing said cells in the presence and/or absence of tumor stroma
administering an agent of interest to said culture
evaluating the effect of said agent on the propagation of said cells in the presence and/or absence of tumor stroma.

A mouse model of human diffuse large B-cell lymphoma (DLBCL), activated B-cell (ABC) subtype, wherein the mouse comprises a population of lymphoma cells as defined in the claims or in paragraphs 1-3 hereinabove is also provided.

In preferred embodiments of the invention, the mouse is a BALB/c mouse. In other preferred embodiments the mouse is an immunocompromised mouse, preferably a $Rag1^{-/-}$ mouse.

SHORT DESCRIPTION OF THE DRAWINGS

FIG. 1. Macroscopic appearance and histopathology of Bc-DLFL.1 lymphoma

Macroscopic pathology (a) reveals significant splenomegaly (arrow) and enlarged mesenteric lymph nodes (mLNs) (arrowhead), with the dotted lines outlining the borders of organs in control mice. Hematoxylin and eosin (H&E) staining of mLN (b; scale bar=200 µm) and spleen (c; scale bar=200 µm) shows lymphoma infiltrate composed of centroblasts intermingled with centrocytes in a representative spleen sample from a BALB/c recipient injected with lymphoma cells (d; scale bar=20 µm).

FIG. 2. Dose-dependence of lymphoma engraftment and mortality

Survival of a cohort of BALB/c mice (n=10 recipients/group) following intraperitoneal injection of lymphoma cells at various doses.

FIG. 3. Immunohistology and cell surface phenotype of Bc-DLFL.1 lymphoma

Anti-B220 staining of a spleen (A) and mLN (B) section from a lymphoma-injected BALB/c mouse reveals a homogenous infiltrate composed of $B220^+$ cells, where in the spleen both the remnants of follicles with more intense B220 expression (arrowhead) and lymphoma (arrow) with a weaker B220 display can be identified (a representative sample from a group of n=8; scale bar=200 µm). (C/1-C/2) A representative flow cytometric staining of lymphoma cells from the mLN a $Rag1^{-/-}$ recipient indicates the expression of B-lineage associated markers and lack of CD3 (n=7). Numbers in the histograms correspond to the cumulative percentage of positive cells in the fluorescence channel range indicated by the horizontal line.

FIG. 4. BcR isotype and IgH V-rearrangement in Bc-DLFL.1 lymphoma (a) B220-positive cells in Rag1$^{-/-}$ recipient mLN sample were stained for cell surface Ig isotypes as indicated, with the mean fluorescence intensities (MFI) shown (n=5), where only IgG2a Ig subclass expression is detectable. (b) PCR analysis of IgH V-region rearrangement demonstrates identical VDJ-rearrangement of $V_H$7183 family in lymphoma-injected BALB/c or Rag1$^{-/-}$ recipient (indicated at the top), with using control BALB/c mLN (NFW, nuclease-free water; n=5).

Figure 5:
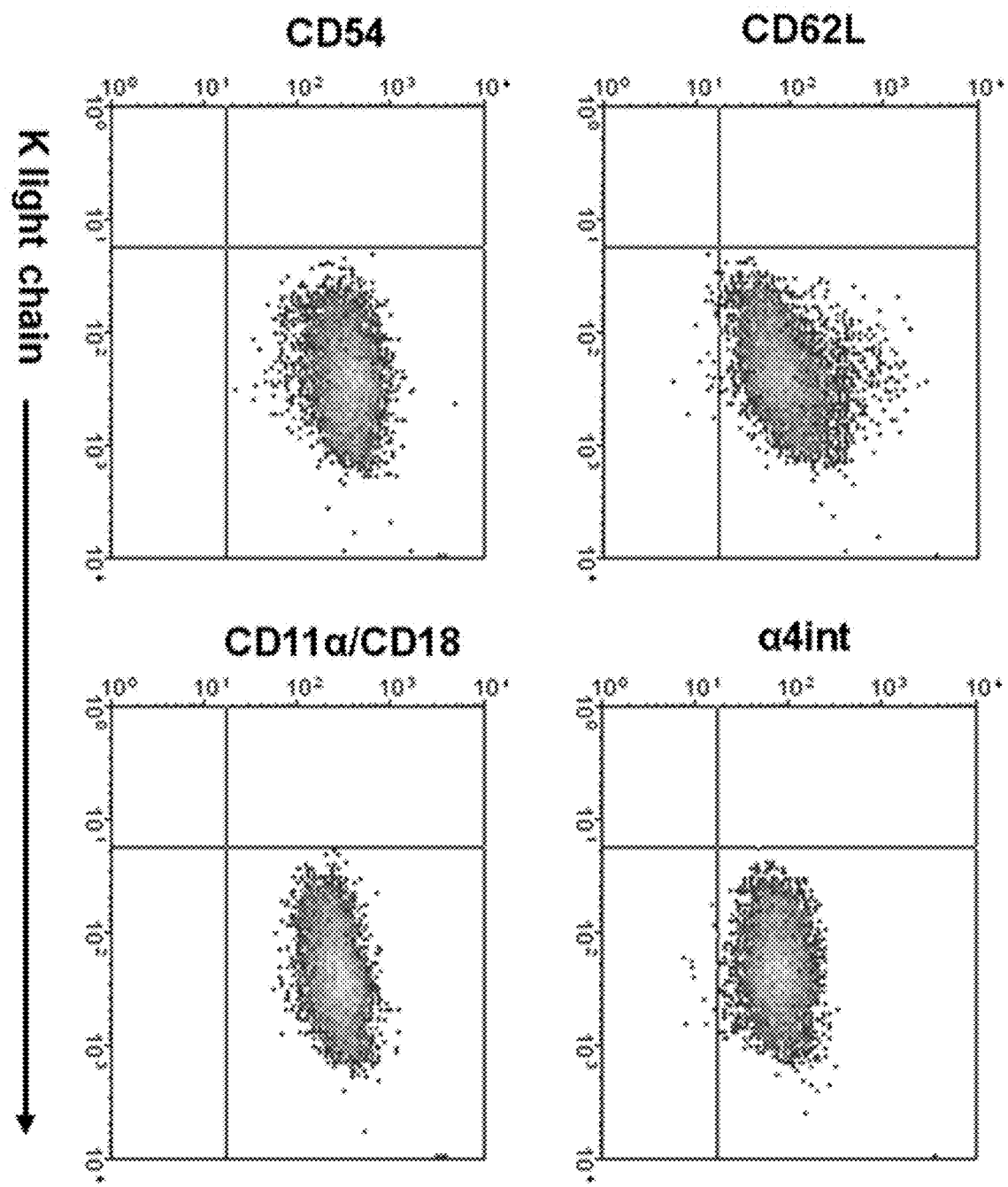

FIG. 5. Adhesion and homing receptor expression by Bc-DLFL.1 lymphoma cells

Lymphoma cells from Rag1$^{-/-}$ recipients' mLN were labeled for various adhesion molecules (indicated at the vertical axis) and surface Ig κ-chain together with B220 staining. Density plots depict the expression of adhesion molecule plotted against surface Ig κ-chain of B220$^+$ lymphocytes (n=7).

Figure 6:
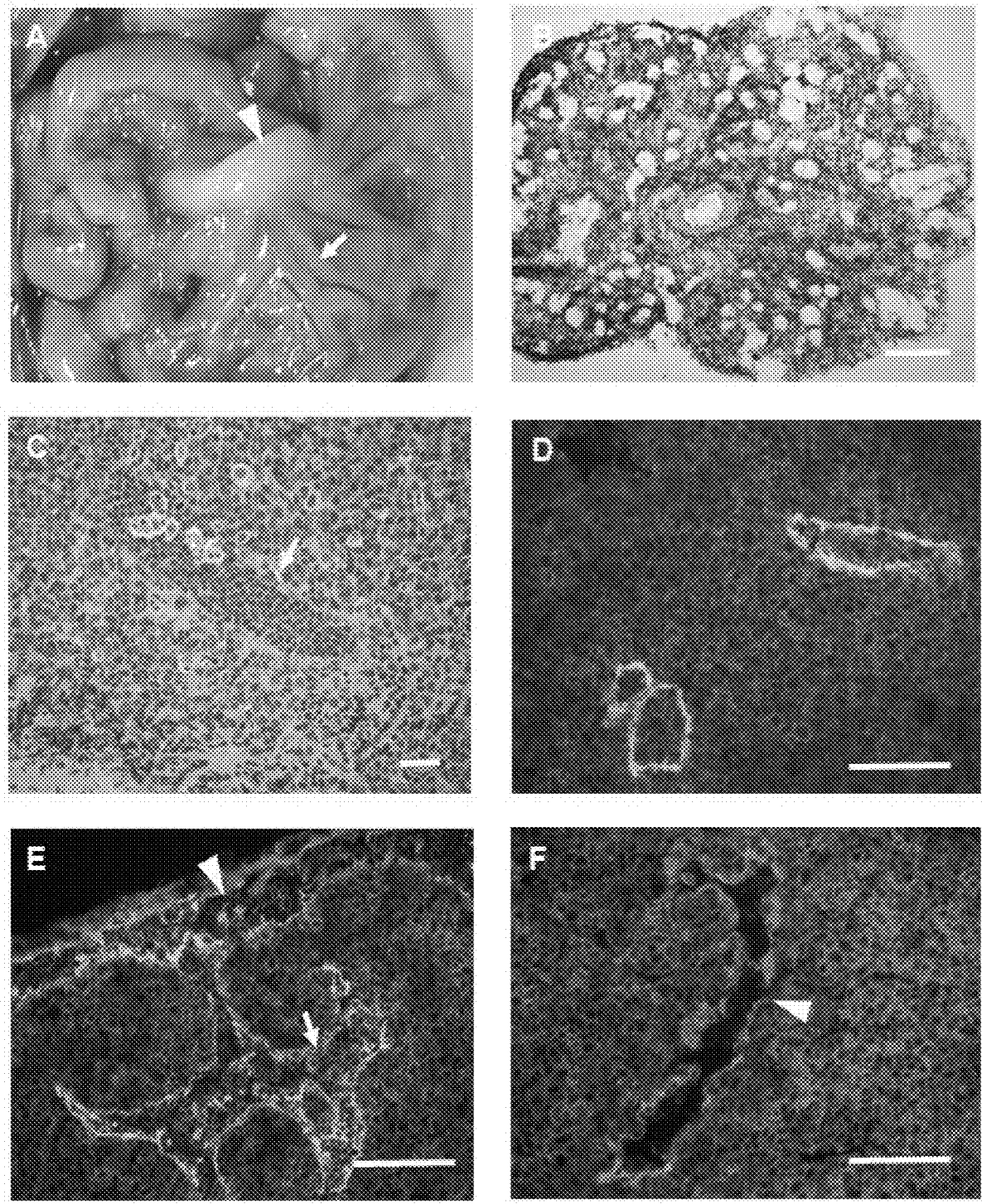

FIG. 6. Mesenteric propagation of Bc-DLFL.1 lymphoma cells involves lymphatic vessels (a) Perivascular spreading in the mesentery (arrow) draining towards the mLN (arrowhead) of Bc-DLFL.1 lymphoma cells in BALB/c recipient following ip. injection involves (b) a compact accumulation of B220-positive lymphoma cells (brown with blue hematoxyline counterstain), also visible in dilated lymphatic vessels (arrow in c; H&E stain). (d) Dual immunofluorescent staining of mesentery for LYVE-1 (green) and B220 (red) shows tight clustering both inside and outside the lymphatic capillaries. (e) mLN section stained for B220 (red) and LYVE-1 also demonstrates numerous lymphoma cells both in the subcapsular sinus (arrowhead) and the corticomedullary lymphatic sinuses (arrow), whereas (f) the PNAd-positive HEVs labeled with MECA-79 mAb (green, arrowhead) are devoid of lymphoma cells (n=5; scale bars=100 μm).

Figure 7:
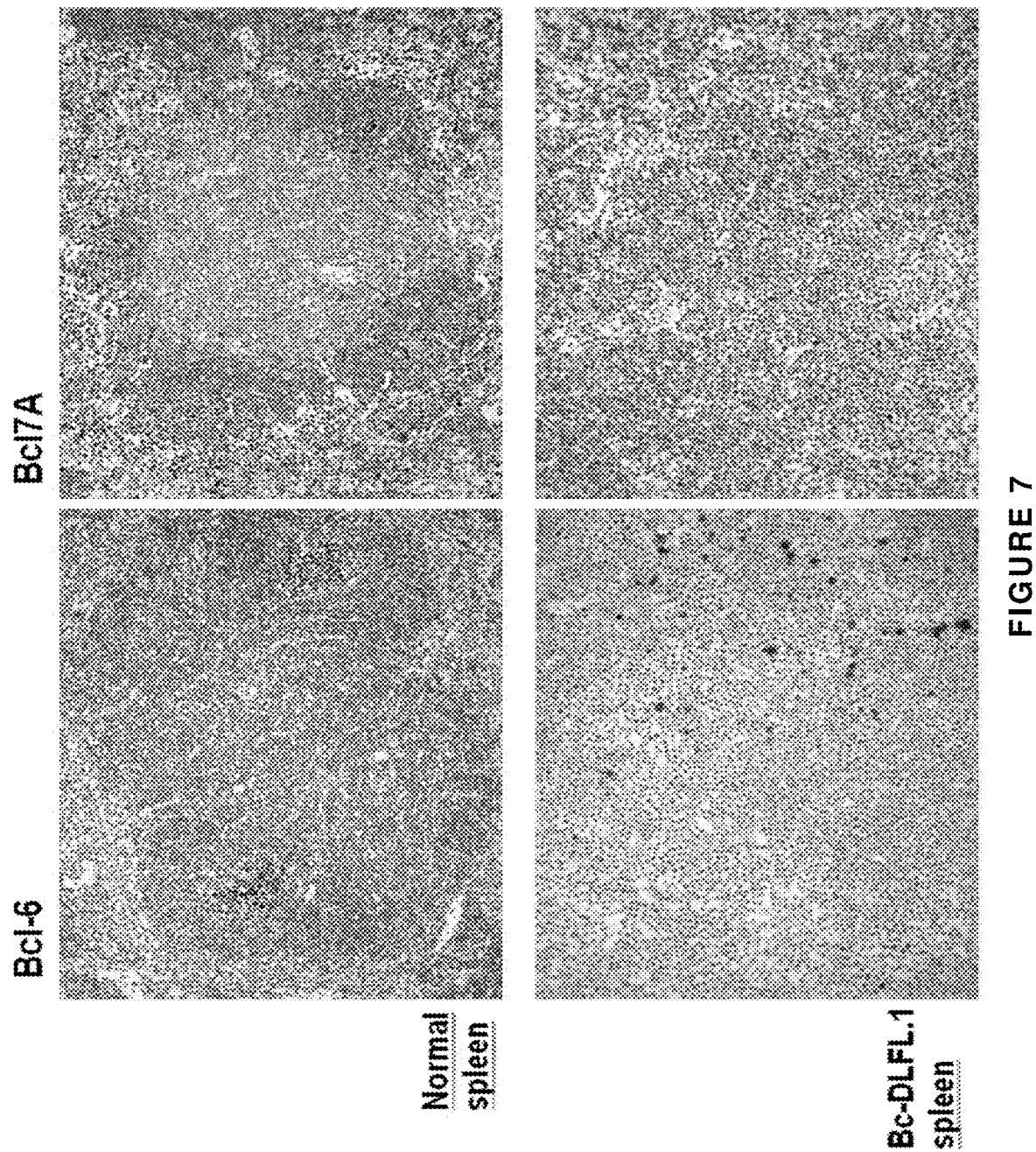

FIG. 7. Immunohistochemical detection of Bcl-6 and Bcl7A expression in normal (control) spleen and in spleen of a mouse with Bc-DLFL.1 cells.

Figure 8:
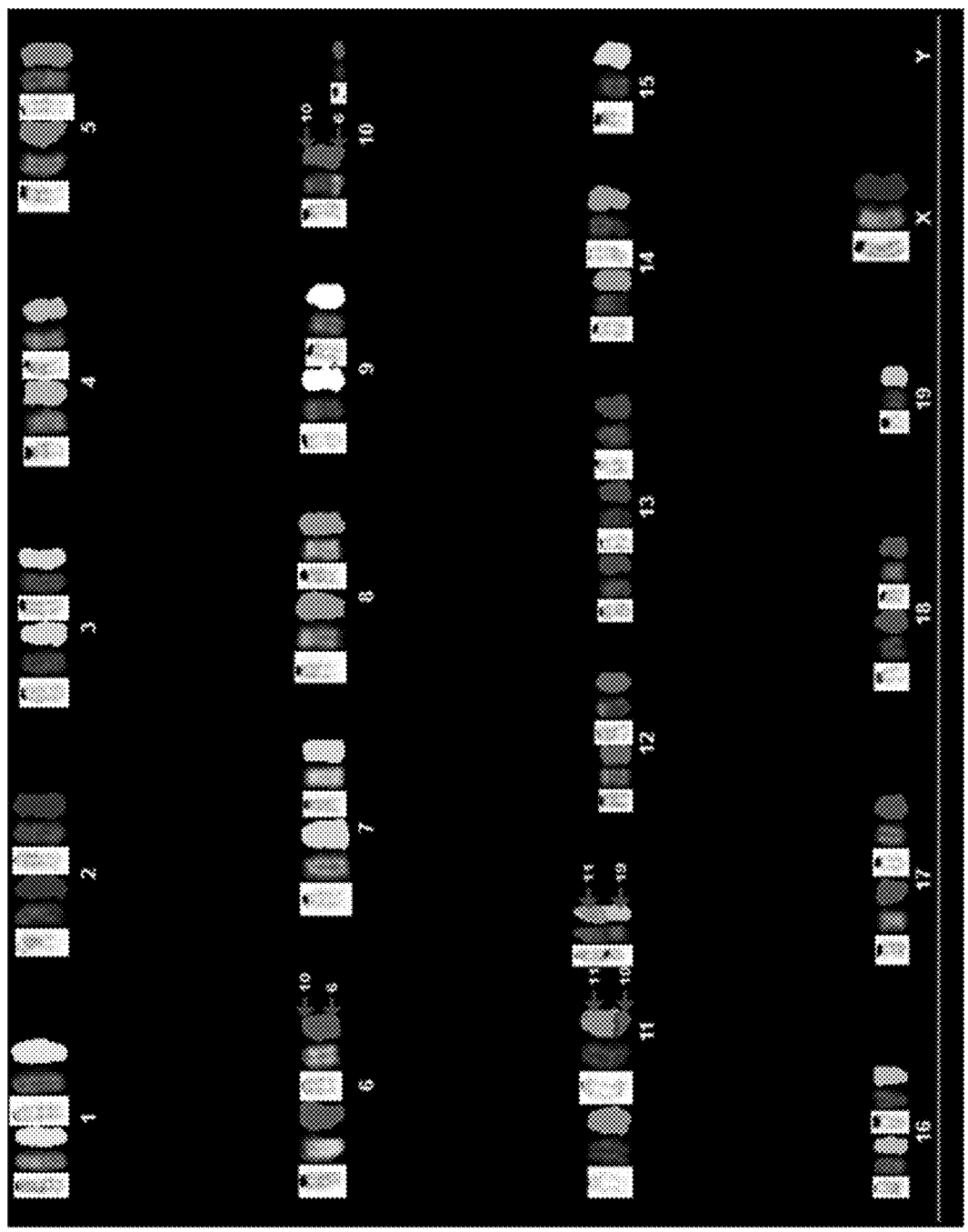

FIG. 8. SKY analysis of karyotype of Bc-DLFL.1 cells.

Figure 9:
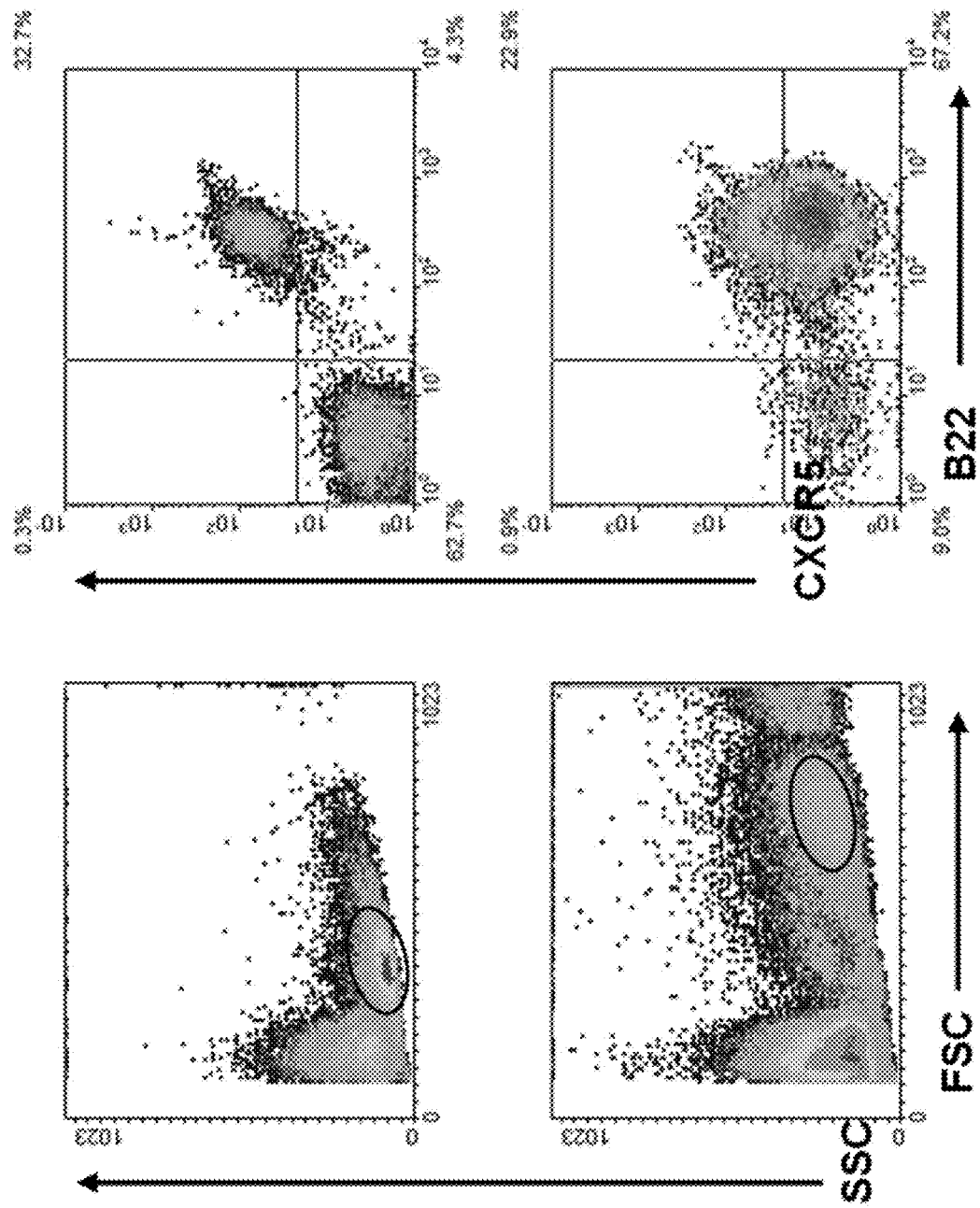

FIG. 9. Lack of CXCR5 expression in Bc-DLFL.1 cells. Live gates are shown as black ellipse on the FSC:SSC plots. Top pair: normal lymph node suspension. Bottom pair: mesenteric lymph node suspension from lymphoma-bearing mouse.

Figure 10A:
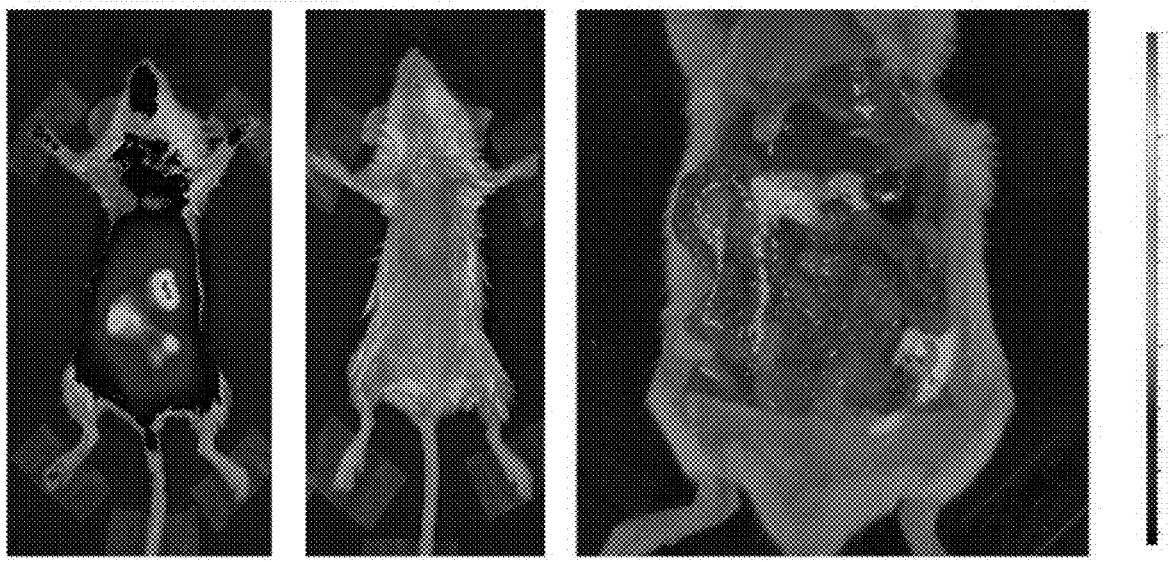
Figure 10B:
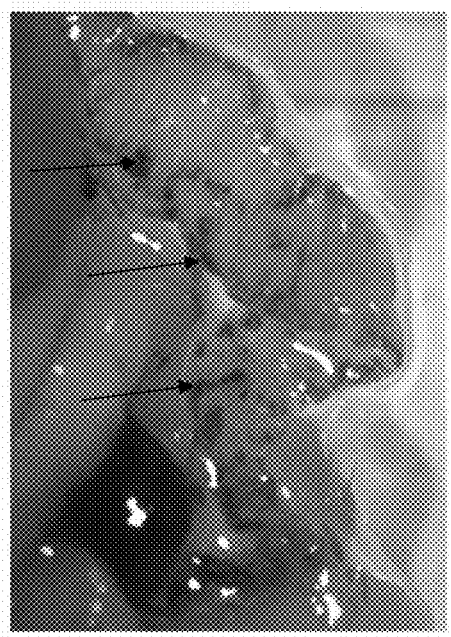
Figure 10C:
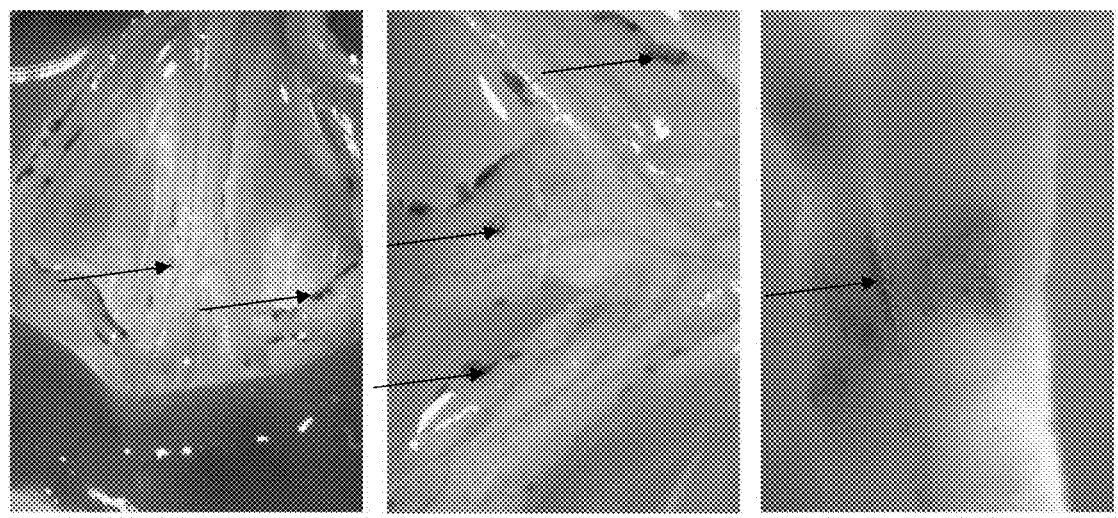

FIG. 10A to FIG. 10C. Fluorescence-based bioimaging and immunohistochemical tracing of labeled lymphoma cells. Arrows on the whole-mounts show clusters of CFSE-labeled cells.

Figure 11:
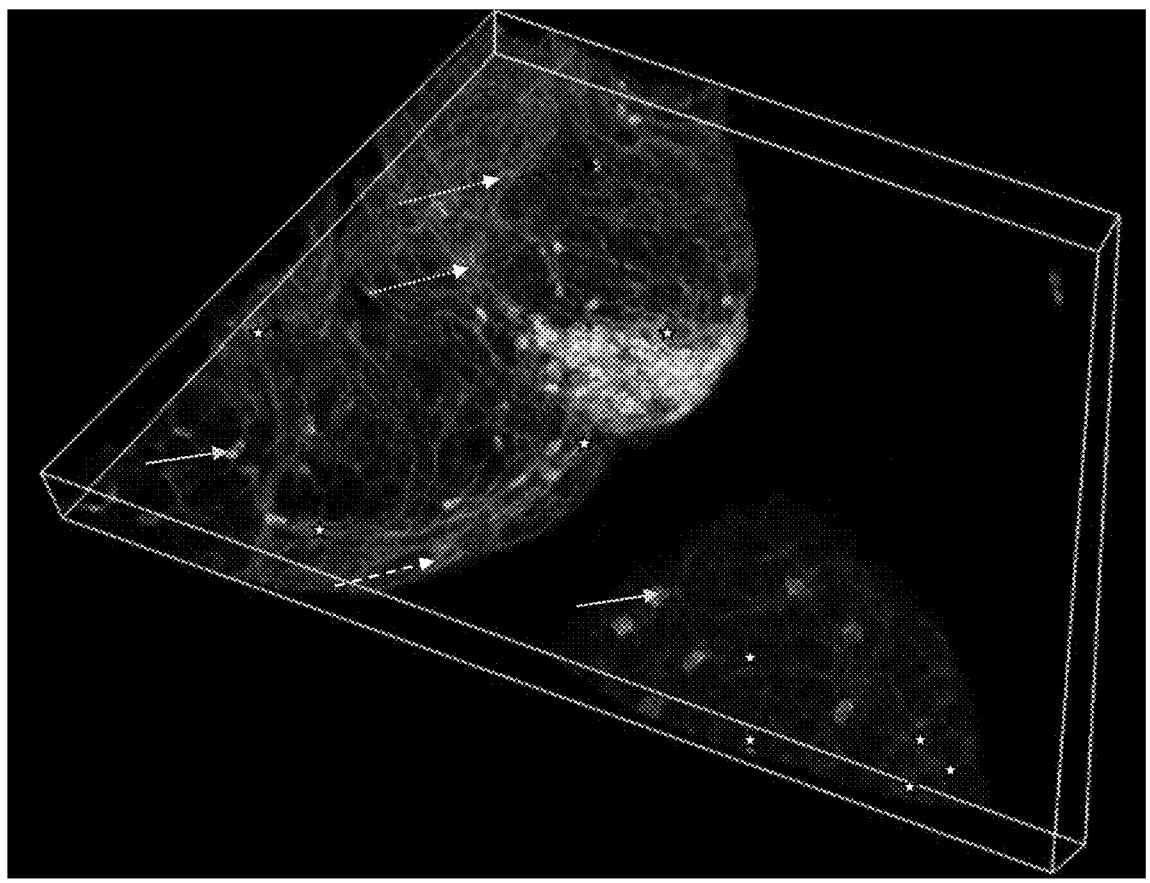

FIG. 11. 3D rendering of mesenteric lymphoma clusters. (Arrows: CFSE lymphoma cells; dotted line: fibronectin; star: LYVE-1, not all cells indicated).

Figure 12:
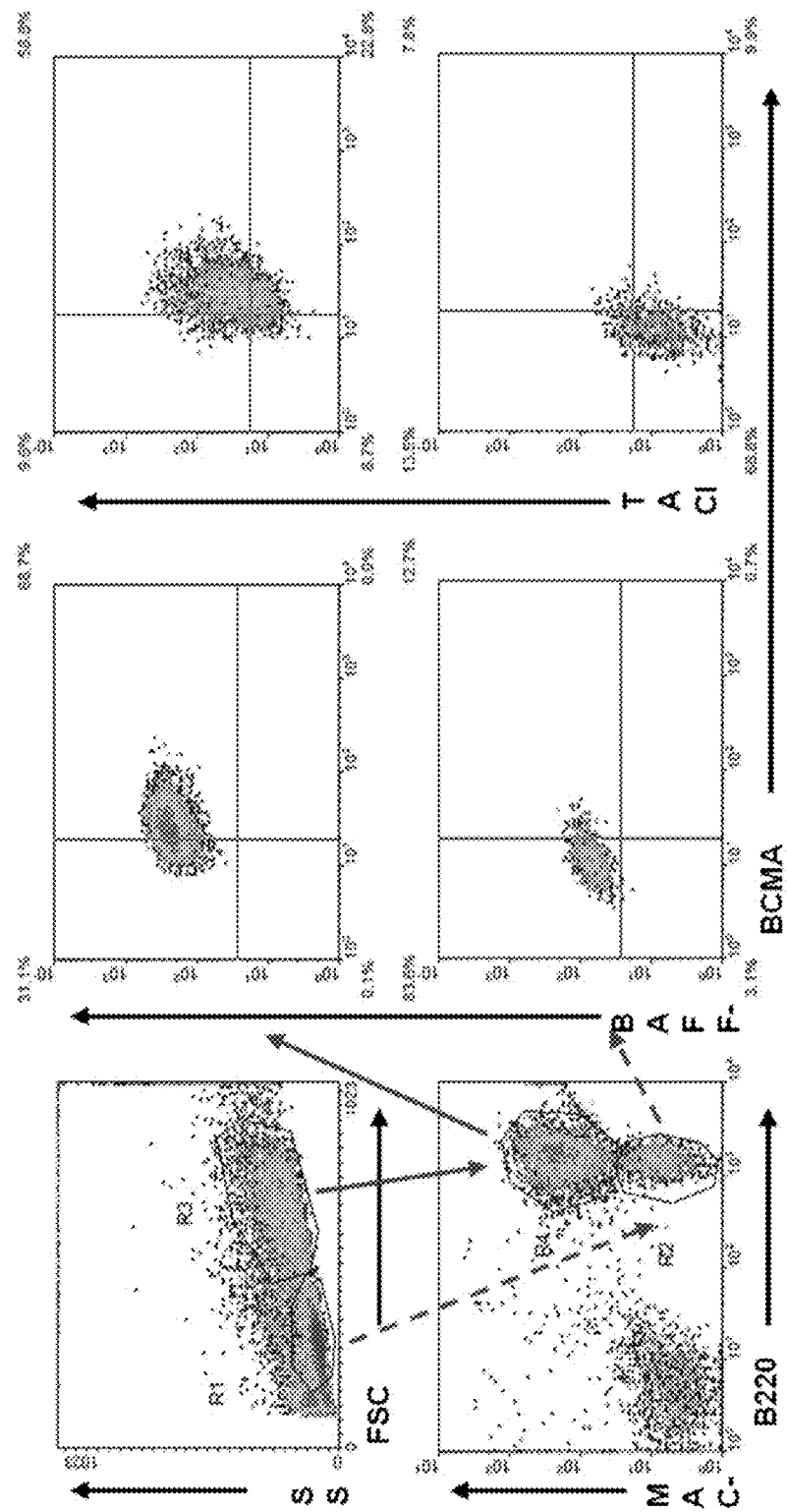

FIG. 12. Expression of BAFF receptors in Bc-DLFL.1 cells. Continuous arrows indicate the gating strategy for the lymphoma cells, dashed arrows indicate the residual B cells.

Figure 13:
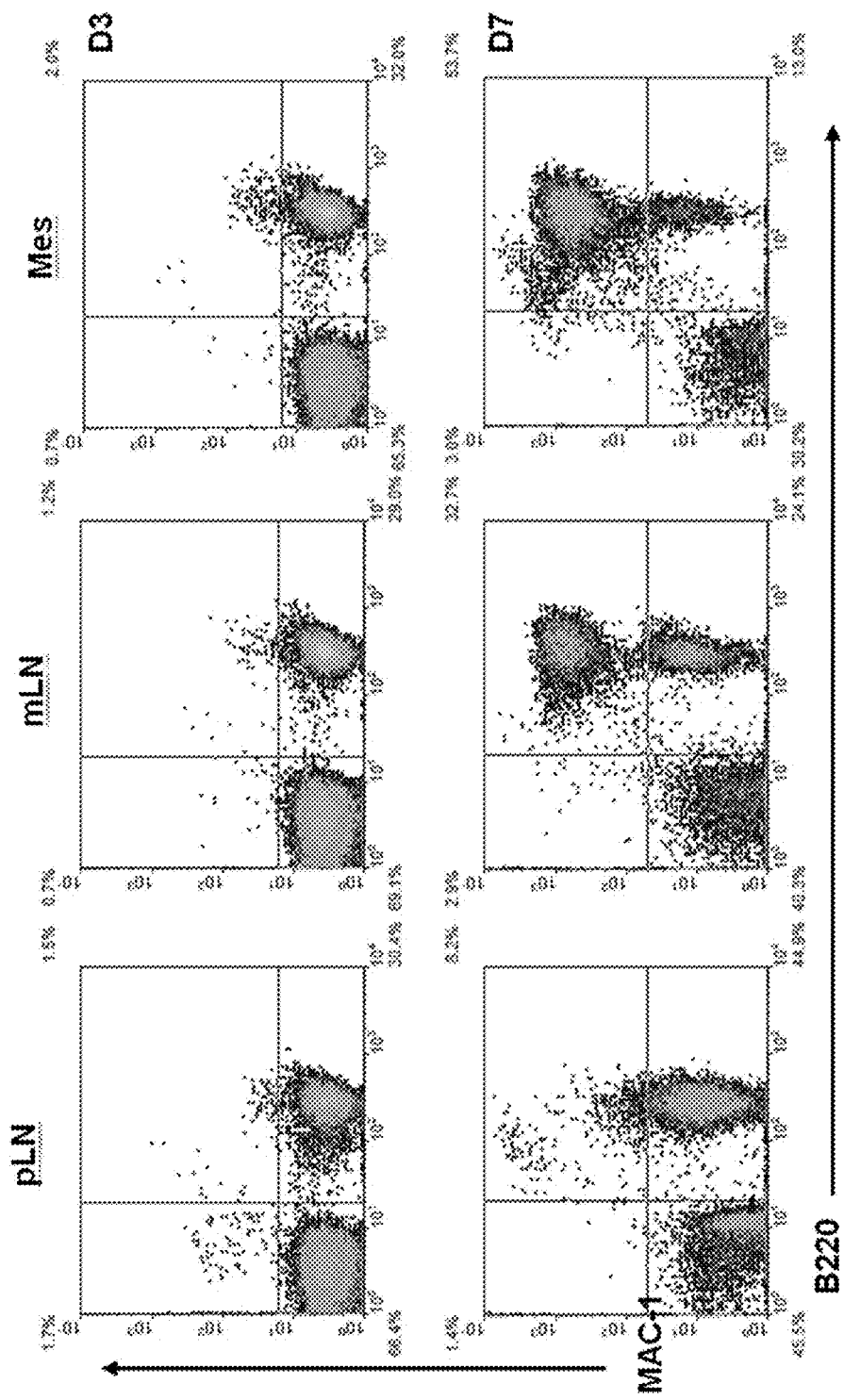

FIG. 13. Representative samples for the comparison of Bc-DLFL.1 cell expansion analysis in various lymphoid organs 3 days (D+) or 7 days (D7) after lymphoma injection ip. pLN: Peripheral lymph node; mLN: Mesenteric lymph node; Mes: Mesenterium.

DETAILED DESCRIPTION OF THE INVENTION

The present inventors have unexpectedly found, isolated and successfully propagated a lymphoma cell line, denoted Bc-DLFL.1, displaying CD19, B220, MHC II, surface IgG2a/kappa chain and MAC-1, indicating B-cell origin. The cells, however, do not express CD5, ruling out B-1a origin. The cells are further characterized by a number of translocation involving chromosomes 6, 10, 11 and 19 as t(10:6), t(6:10), t(11:19) and t(10:11) chromosomal translocation. Although the lymphoma showed characteristics of a malignancy that may be correlated to human indolent diffuse large B-cell lymphomas, further studies revealed very unusual properties, such as restricted and time dependent tissue distribution, marker pattern and propagation conditions. As used herein, the term "lymphoma cell" refers to a B-lineage cell arising after malignant transformation.

Based on the results, a new lymphoma cell line and a laboratory tool for the assessment of B-cell lymphoma expansion and normal B-cell migration, for the assessment of in vivo tumor microenvironment in an in vitro method are provided. For example the role of FALC (fat associated lymphoid clusters) located along the blood vessels in the mesentery and/or of milky spots in the omentum in lymphoma/B-cell homing may be assessed using the cells according to the invention, because these cells show an extensive accumulation of lymphoma within short time after administration without a significant amount of cells outside these regions within the same time frame. Bc-DLFL.1 cells expand rapidly in a recipient mouse, but the migration is highly specific as described herein and due to the specific marker pattern, the cells may be identified reliably. Assessment of agents affecting the lymphoma-tumor microenvironment cooperation will also benefit from the use of Bc-DLFL.1. Agents of interest may be e.g. agents produced by the tumor microenvironment (i.e. stroma), e.g. cytokines, growth factors and the like or compounds to be tested for their anti-tumor or pro-tumor activities. Studies may be performed either in vivo or in vitro, as animal models of B-cell lymphoma are also provided. According to the studies of the inventors, histologic and cytopathological features of the lymphoma are preserved even after serial propagation.

A BALB/c mouse-derived novel spontaneous B-cell lymphoma has been isolated and characterized. The intraperitoneal injection of this lymphoma has resulted in a selective tumor seeding of the omentum and the fat associated lymphoid clusters located along the blood vessels in the mesentery, followed by a delayed colonization of the spleen and mesenteric lymph nodes in the moribund state. The metastasis has been formed via the lymphatic vasculature of mesentery. Thus this novel B-cell lymphoma offers a unique model for studying the in vivo lymphatic propagation of B-cell tumors. Additionally, unlike the majority of other mouse lymphoma models, this tumor arose without any previous induction, such as viral or other microbial infection, exposure to chemical carcinogens, or employing genetic manipulation by introducing mutated proto-oncogenes or other regulatory elements, therefore its origin is closer to the human conditions.

Serial intraperitoneal injection of the primary tumor into both BALB/c and RAG-1-deficient hosts led to the successful propagation of lymphoma. Despite the cytological characteristics of high-grade follicular B-cell lymphoma, the tumor cells showed significantly lesser spreading to extraabdominal locations upon intraperitoneal passage compared to expansion into the omentum and the FALC located along the blood vessels in the mesentery, and later, splenic and mesenteric lymph node expansion. In mesenteric lymph nodes the high endothelial venules contained only few tumor cells, while the lymphatic vessels were almost completely filled with lymphoma cells. Similarly, the LYVE-1-positive lymphatic capillaries within the mesentery were packed with lymphoma cells. Accordingly, the lymphoma shows restricted tissue distribution and metastasis, depending on tissue type and time.

Culturing the tumor cells in vitro and in vivo. A population of cells according to the invention may be provided by in vivo propagation, in vitro culturing and/or the combination of steps of propagation in vitro and in vivo. For in vitro propagation, culture media suitable for B-lineage cells is required. Media for B-lineage cells are numerous and are commercialized by well-known suppliers, such as Sigma, Biological Industries, ATCC, etc. The different culture media may require different supplementation or conditions, which may be determined by the manufacturer. Cell culture techniques are within the skills of the skilled person. Such methods can be found in various textbooks, see e.g. [27]. General purpose culture media, such as different types of Dulbecco's modified Eagle's media (DMEM) may be used. Typically, DMEM has almost twice the concentration of amino acids and four times the amount of vitamins as Eagle's Minimum Essential Medium, as well as ferric nitrate, sodium pyruvate, and some supplementary amino acids. A variation with 4500 mg/L of glucose has been proved to be optimal for culture of various types of cells. DMEM is a basal medium and contains no proteins or growth promoting agents. Therefore, it requires supplementation to be a "complete" medium. It is most commonly supplemented with 5-10% Fetal Bovine Serum (FBS). DMEM utilizes a sodium bicarbonate buffer system (3.7 g/L) and therefore requires artificial levels of $CO_2$ to maintain the required pH. Typical composition of the culture medium for the cells according to the invention may be 10% DMSO, 20% fetal bovine serum (FBS), 70% DMEM. Growth conditions may include 37° C. and 5% $CO_2$. Antibiotics such as penicillin (e.g. 100 IU/ml) or streptomycin (e.g. 0.1 mg/ml) may be added.

RPMI and its variations are general purpose media with a broad range of applications for mammalian cells, especially hematopoietic cells. RPMI-1640, for example, was developed for the long-term culture of peripheral blood lymphocytes. RPMI-1640 uses a bicarbonate buffering system and differs from the most mammalian cell culture media in its typical pH 8 formulation. RPMI-1640 supports the growth of a wide variety of cells in suspension and grown as monolayers. For culturing B-lineage cells, RPMI-type media, e.g. RPMI-1640 are usually supplemented with 10% fetal bovine serum or autologous serum. The cells of the invention may be propagated in RPMI, such as RPMI-1640, supplemented with 10% FBS, and antibiotics, such as penicillin (e.g. 100 IU/ml) or streptomycin (e.g. 0.1 mg/ml). The culture medium may be supplemented and prepared differently, according to the manufacturer's instructions.

A cell culture of the cells according to the invention may be prepared as follows: inoculating mice with the cells according to the invention, isolating and dissecting the removed organ affected by the lymphoma (e.g. mesenteric lymph node), mechanically releasing the lymphoma cells using a cell strainer, initiating cultures from the washed/stroma-containing fraction retrieved from the strainer (e.g. in RPMI supplemented by 10% fetal bovine serum) and adding the washed lymphoma cells. Although inoculation with Bc-DLFL.1 cells results in high and rapid mortality (within 12-14 days when an amount of $2.5 \times 10^6$-$2.5 \times 10^7$ cell/recipient mouse is administered intraperitoneally) the tumor cells can only transiently be propagated in vitro. The growth of the tumor cells is dependent on the parallel expansion of stromal cells. Growth can be promoted on cell culture trays covered with a layer of tumor stroma. If the lymphoma cells are separated after the early phase of stromal cells sedimenting and adhering, thus reducing the stromal components, then they mostly die in 2-3 days. Hence the stromal elements are necessary for keeping the cells survivable until they are ready to be reinjected into recipient mice. However, lymphoma cells maintaining contact keep growing and form grapelike agglomerates.

"Tumor stroma", "stroma cells", "stromal elements". By stroma the supportive framework of a tissue is meant, which can be transformed by tumor cells. Both normal and tissue stroma contain different types of cells and extracellular elements. "Tumor stroma" as used herein refers to the stromal elements of the tumor environment in vivo. Tumor stroma may be derived from the lymphoma bearing animal together with the lymphoma. In the culture methods according to the invention, preferably the original, from the animal derived stromal microenvironment of the lymphoma is used as tumor stroma.

Transient propagation is possible in RPMI (e.g. RPMI-1640)+10% fetal bovine serum. Growth conditions include 37° C., 5% $CO_2$ and humidity (standard cell culture conditions). The medium can be changed at 1/3 ratio (1/3 remaining, 2/3 new medium added). Typical composition of the culture medium may be 10% DMSO, 20% fetal bovine serum, 70% DMEM (Dulbecco's modified Eagle's medium). Antibiotics such as penicillin (e.g. 100 IU/ml) or streptomycin (e.g. 0.1 mg/ml) may be added.

Thawed cells after overnight culture can be propagated by intraperitoneal injection where the injected mice will develop the original lymphoma in their mesenteric lymph nodes and spleen in 14-18 days.

Symptoms of the developed lymphoma are usually evident even without dissecting the animal. The enlargement of the spleen is apparent in moribund mice.

Bc-DLFL.1 lymphoma cells cultured by the method described above have been deposited at the Deutsche Sammlung von Mikroorganismen and Zellkulturen (DSMZ) on Sep. 24, 2015 under the number DSMZ ACC3278.

The specific conditions needed for in vitro growth indicate that the Bc-DLFL.1 cell line is a suitable tool to study stroma-tumor cell relationship in vitro and in vivo.

Characterization of the tumor and the tumor cells. The original tumor was found in a BALB/c mouse as a robust splenomegaly and a soft tissue mass surrounding the terminal segment of the ileum. Macroscopic gross pathology could not have been detected in the abdominal organs, lungs and brain and also peripheral lymph nodes (inguinal, cervical and brachial) and Peyer's patches. Single cell suspensions of the original enlarged spleen injected ip. in BALB/c recipients caused similar phenomena to the original tumor-bearing mouse, i.e. enlarged mesenteric lymph nodes (mLN) and spleen (FIG. 1a). Tumor cells could be passaged serially in vivo and cultured in vitro. Bc-DLFL.1 lymphoma cells could efficiently be propagated in both syngeneic BALB/c and allogeneic $Rag1^{-/-}$ recipients. Both the in vivo passaged and in vitro cultured cells reserved their characteristics and induced lymphomagenesis in recipient animals. Injecting large number of cells ($2.5 \times 10^7$ and $2.5 \times 10^6$ cells in each recipient) could uniformly lead to death within 15 days ($p<0.001$), and even $2.5 \times 10^5$ cells/recipient were sufficient to induce 50% mortality in BALB/c recipients (FIG. 2) within 30 days ($p<0.01$).

Further studies identified chromosomal translocations (t(10:6), t(6:10), t(11:19) and t(10:11)), the presence of CD19, B220, MHC II, surface IgG2a/kappa chain and MAC-1, the lack of CD3 expression and CD5 production.

The presence of BAFF-R, BCMA and TACI has been confirmed. Cytometric analysis has shown the presence of Bcl-6, later indirect immunohistochemistry found no detectable Bcl6 expression at a level displayed by normal splenic centroblasts. Expression of Bcl7A was detectable by the same method. The cells are mostly negative or only weakly positive for CXCR5.

It was found, that the Day 7:Day 3 ratio of MAC-1/B220 double positive cells in the total lymphocyte population was highest in the mesenteric lymph nodes and mesenterium followed by the spleen (5.9×) and least in the peripheral lymph nodes.

Due to the specific pattern of cell surface markers on the lymphoma cells according to the invention, it is possible to identify the different cells (e.g. in a lymph node or other affected organ) by incubating the cells with a cocktail of labeled anti-CD19, anti-CD5, anti-MAC-1 and anti-B220 antibodies. Cell populations will be stained as shown in Table 1.

TABLE 1

| Cell population | CD5 | CD19 | MAC-1 | B220 |
| --- | --- | --- | --- | --- |
| T cells | + | − | − | − |
| Normal B1a cells | − | + | − | + |
| Lymphoma B cells | − | + | + | + |

For example, lymphoma cells may be incubated with a cocktail of FITC-labeled anti-CD19 (clone 1D3), PE-labeled anti-CD5 (clone 53_7.3), biotinylated anti-MAC-1 (clone M1/70), and Alexa-647 labeled anti-B220 (clone RA3-6B2), followed by incubation with Streptavidin-PE-Cy5 conjugate. After washing the cells are fixed with formaldehyde and analyzed by flow cytometry.

Identification of a cell displaying CD19, B220, MHC II, surface IgG2a/kappa chain and MAC-1, which is negative for CD5. Methods for the identification of cell surface markers are well known in the art Immunohistochemical staining with antibodies against MAC-1, CD19, B220, MHC II molecules, IgG2a/kappa chain and other markers are commercially available (e.g. from Abcam, Sigma Aldrich, etc.) or may be produced in-house. Detection of bound antibodies may be performed by e.g. flow citometry. A non-limiting description of the detection and identification of said markers can be found in the Examples section. Textbooks on immunohistochemistry are e.g. [28].

Animal models according to the invention. It is possible to use the cells according to the invention to generate animal models of human (high-grade) diffuse large B-cell lymphoma (DLBCL), activated B-cell (ABC) subtype. Such an animal model is useful for the in vivo evaluation of an agent or a therapeutic treatment for the treatment of lymphoma and/or prevention of proliferation of lymphoma cells. Due to the specific cell surface marker pattern of the cells according to the invention, it is possible to investigate tumor cell migration (tumor expansion) in vivo in an animal model according to the invention. To generate a mouse model, lymphoma cells according to the invention may be administered to a mouse, preferably a BALB/c or an immunocompromised mouse intraperitoneally in a dose of $10^4$ to $2\times10^5$ cells/recipient, preferably $10^6$ to $5\times10^6$ cells/recipient.

In vitro models according to the invention. The cells according to the invention are useful models for the in vitro evaluation of an agent or a therapeutic treatment for the treatment of lymphoma and/or prevention of proliferation of lymphoma cells. The specific conditions necessary for in vitro growth indicate that the Bc-DLFL.1 cell line is a suitable tool to study stroma-tumor cell relationship in vitro and to test whether an agent affects this relationship. Agents affecting lymphoma and/or normal B-cell expansion/migration may also be studied in an in vitro model using the population of lymphoma cells of the invention.

EXAMPLES

Materials and Methods

Mice

Inbred BALB/c and Rag1−/− [10] mice were originally purchased from Jackson Laboratory, and were maintained under SPF conditions at the Department of Immunology and Biotechnology under permits BAI/01/1390-003/2013 (issued by the Baranya County Government Office) and SF/688-18/2013 and SF/27-1/2014 (issued by the Ministry of Agriculture). After their retrieval from the SPF unit the mice were kept under clean conditions with 12 hours of light/dark cycles and were provided with water and pelleted food ad libitum.

Lymphoma Cell Isolation and Passage

The original tumor was mechanically dispersed using a 70 μm cell strainer (BD Biosciences, Soft Flow Ltd, Pécs, Hungary) and resuspended in DMEM medium (Sigma-Aldrich, Budapest). The tumor cells at the dose of $10^7$ cells/recipients in 0.2 ml medium were injected intraperitoneally. For tumorigenicity testing various doses of lymphoma cells were injected intraperitoneally and the mice were observed daily up to 30 days. Mice with terminal stage tumor were sacrificed by cervical dislocation, and their lymphoid and other organs were collected under aseptic conditions in a laminar flow. For further passage mesenteric lymph node (mLN) and spleen were collected and processed by mechanical dispersion through 70 μm mesh size cell strainer (BD Biosciences (Soft Flow Hungary, Pecs).

Antibodies and Reagents

Rat mAb against MHC Class II (IBL-5/22) was produced in our lab [11] and was used as hybridoma supernatant. mAb against peripheral lymph node addressin (PNAd, clone MECA-79) was purchased from BD Biosciences (Soft Flow Hungary, Pécs), anti-LYVE-1 (clone 223322) and goat anti-mouse Bcl-6 antibodies from R&D Systems (Biomedica Hungária Kft, Budapest). Anti-mouse VEGF-R2/flk-1 mAb (clone Avas12α1) was purchased from BD Biosciences. Anti-mouse CD19 (clone B3B4), anti-mouse CD3 (clone KT-3), anti-mouse LFA-1 (clone M14.4) and anti-mouse L-selectin/CD62L (clone MEL-14) and anti-mouse ICAM-1/CD54 (clone YN1/1) and anti-MAC-1 (clone M1/70) hybridoma lines were obtained from ATCC, anti-α4 integrin mAb (from clone PS/2) was kindly provided by Dr. Eugene C. Butcher. Anti-B220 IgG (clone RA3-6B2 from ATCC) was purified by Protein G chromatography and labeled with FITC or Alexa Fluor 568 dye (Life Technologies Magyarorszag Kft, Budapest) using standard labeling conditions or used as hybridoma supernatant. FITC-conjugated anti-mouse IgM, IgG1, IgG2a, IgG2b and IgA rabbit antibodies were purchased from Sigma-Aldrich. Control rat IgG was purified from Wistar rat serum using Protein G affinity chromatography. The unlabeled rat mAbs and the goat polyclonal antibodies were detected with goat anti-rat IgG or donkey anti-goat IgG respectively, conjugated with FITC or PE (BD Biosciences). For immunohistochemical staining the anti-B220 mAb was detected by Histols polymeric anti-rat IgG HRPO-conjugate (Hisztopatologia Kft, Pécs, Hungary).

Flow Cytometry

Single cell suspension prepared from mLN, peripheral lymph nodes (pLN) or spleen of Rag1−/− or BALB/c recipients were incubated with monoclonal antibodies against MHC Class II, CD3, CD19, B220 or normal rat IgG and various anti-mouse immunoglobulin isotype antibodies at 10 μg/ml in PBS containing 0.1% Na-azide and BSA for 30 minutes followed by two washing steps. The bound antibodies were detected using FITC-conjugated goat anti-rat IgG, followed by washing. The cells were fixed in 1% buffered paraformaldehyde and the samples were analyzed using a Becton-Dickinson FACSCalibur and the CellQuest Pro software. Typically ten thousand single lymphocyte events as defined by their FSC/SSC characteristics were collected.

Histology and Immunohistology

Formol-fixed and paraffin embedded tissues (spleen, mesenteric lymph nodes and mesenterium, thymus, peripheral lymph nodes, liver, kidney, lungs and brain) were processed according to standard histological procedures using hematoxylin-eosin and periodic acid-Schiff staining. For immunohistochemical or immune-fluorescent labeling tissues were placed in Killik embedding medium and snap-frozen in plastic molds. Frozen sections at 8 μm thickness were cut with a Leica cryostat and placed onto microscopic slides, and were allowed to dry. After fixing in cold acetone the sections were allowed to dry. The endogenous peroxidase activity was quenched with 0.1% phenyl-hydrazine hydrochloride in PBS for 20 minutes followed by washing. After blocking with 5% BSA in PBS for 20 minutes anti-B220 antibody was added and incubated for 4 minutes. After washing polymeric Histols anti-rat IgG-HRPO conjugate was added and incubated for 45 minutes. After repeated washing the enzymatic reaction was developed using DAKO acetate buffer and diamino-benzidine solution, and mounted using Permount medium.

For dual immunofluorescence after fixation in acetone the slides were allowed to dry, and then rehydrated in 5% BSA-PBS. Next the sections were incubated either with anti-LYVE-1 or anti-PNAd mAbs, followed by FITC-conjugated goat anti-rat IgG. After washing the residual binding sites of the secondary antibody were saturated with normal rat serum at 1:50 dilution for 20 minutes, followed by adding Cy3-conjugated anti-B220 mAb. After incubation the sections were repeatedly washed in PBS and covered in 1:1 PBS-glycerol, and viewed under Olympus BX61 fluorescent microscope.

The mesenteric location of tumor cells was determined by labeling the cells with either XenoLight DiR lipophilic dye or CFSE (5(6)-Carboxyfluorescein N-hydroxysuccinimidyl ester). DiR fluorescence was detected by FMT 4000 In Vivo Imaging System with 710(ex)/760(em) filter set, CFSE-labeled cells were revealed by immunohistochemistry of whole-mount mesenteric samples using HRP-conjugated anti-FITC or multifluorescent labeling for LYVE-1 lymphatic endothelium and fibronectin 24 to 72 hours following intraperitoneal injection of $2 \times 10^5$ labeled lymphoma cells.

The in vivo tissue distribution of Bc-DLFL.1 lymphoma cells was monitored by dual staining for MAC-1 and B220 followed by the flow cytometric evaluation of various lymphoid tissues (inguinal lymph nodes, mesenteric lymph nodes, mesenterium and spleen) at days 3 and 7 after the cell transfer.

The expression of Bcl6 and Bcl7A was determined by indirect immunohistochemistry using 4B2 anti-mouse Bcl6 and 15C anti-Bcl7A monoclonal antibodies on formaldehyde-fixed and paraffin-embedded tissue sections from mesenteric lymph nodes and spleen from control and lymphoma-bearing mice.

Cytogenetic Alterations

The cytogenetic characterization for modal chromosome number and translocation pattern was performed by SKY spectratypic analysis and Giemsa chromosomal staining at the Department of Genetics, University of Texas M. D. Anderson Cancer Center, Houston, USA.

Analysis of IgH Rearrangement

DNA from $2 \times 10^5$ lymphoma cells was extracted using Qiagen QIAamp DNA Micro Kit according to the user's instructions. The rearrangement status of Ig heavy chain gene was determined by PCR reaction using degenerate primers for various murine VH families as described [12]. The amplified products were electrophoresed and visualized using Biotium GelRed. The images were recorded using Bio-Rad Gel Doc XR instrument and Image Lab 5.0.0 software.

Expression of BAFF Receptors Variants (BAFF-R, TACI and BCMA) and CXCR5

The expression of BAFF receptors variants (BAFF-R, TACI and BCMA) and CXCR5 was determined by flow cytometric analysis.

Statistical Analysis

Survival data for Kaplan-Meier evaluation were statistically analyzed by logrank (Mantel-Cox) test using GraphPad Prism software.

Identification of the Spontaneous High-Grade B-cell Lymphoma

As an incidental finding during the dissection of an aged BALB/c female mouse a soft tissue mass was found surrounding the terminal segment of ileum, accompanied with a robust splenomegaly. Macroscopic observation of the abdominal organs, lungs and brain and also peripheral lymph nodes (inguinal, cervical and brachial) and Peyer's patches did not reveal any gross pathology. To test whether the splenic enlargement may be caused by lymphohematopoietic malignancy the enlarged spleen was removed and single cell suspension was injected intraperitoneally into a cohort of BALB/c recipients. The injected mice showed a sharp decline of physical activities at around 15-18 days after the injection, and after sacrificing the moribund mice we observed enlarged mesenteric lymph nodes (mLN) and spleen, similar to the original tumor-bearing mouse (FIG. 1a). The tumors were removed and processed for serial in vivo passage as well as cryopreservation. Histological sections prepared from the mLN and spleen showed a vaguely nodular lymphoid infiltrate composed of centroblast and centrocyte-like atypical cells showing brisk mitotic activity. The ratio of centroblast-like cells was heterogeneous, on average approximately 40%. The infiltrate replaced the follicles and extended in other lymphoid regions (FIG. 1 b/c/d). PAS staining revealed no positive labeling for the lymphoma cells (not shown). The splenic white pulp and the mLN contained homogenously B220-positive lymphoma cells, although at some locations within the splenic white pulp some remnants of the original follicles could be found, based on their more intense B220 expression (FIG. 3a/b).

In both syngeneic BALB/c and allogeneic Rag1$^{-/-}$ recipients the tumor cells could efficiently be propagated. We found that injecting large number of cells ($2.5 \times 10^7$ and $2.5 \times 10^6$ cells in each recipient) could uniformly lead to death within 15 days (p<0.001), and even $2.5 \times 10^5$ cells/recipient were sufficient to induce 50% mortality in BALB/c recipients (FIG. 2) within 30 days (p<0.01).

Given the relative frequent appearance of B-cell derived malignancies in aged BALB/c mice [13], to define the hematopoietic lineage affiliation of the tumor we performed immunohistochemistry using B220 as a B-cell antigen. We found that both the splenic white pulp and the mLN contained homogenously B220-positive lymphoma cells, although at some locations within the splenic white pulp some remnants of the original follicles could be found, based on their more intense B220 expression (FIG. 3a/b). To further verify the B-cell origin of this spontaneous lymphoma we performed flow cytometric phenotyping using CD19 and MHC Class II labeling, using B220 as reference marker in tumor cell suspension obtained from Rag1$^{-/-}$ recipients. To rule out T-cell malignancy we also labeled the cells for CD3 and CD5. Positive reactivity for CD19, MHC class II, in addition to B220 and the lack of CD3 expression and CD5 production (not shown) confirmed our earlier immunohistochemical results for B220 expression, thus establishing the B-cell origin of this lymphoma (FIG. 3c). Lymphoma cells also showed positive reactivity to MAC-1. Taken together the B-lineage surface markers with the cytological characteristics, this lymphoma corresponds to human high-grade B-cell lymphoma (DLBCL), unclassifiable cell of origin (non-germinal center [nGCB] or activated B cell [ABC]) subtype [22].

Cytogenetic Alterations

Chromosome staining of Bc-DLFL.1 cells revealed 39-41 chromosomes, typically 40/XX. SKY analyses revealed a number of translocation involving chromosomes 6, 10, 11 and 19 as t(10:6), t(6:10), t(11:19) and t(10:11) [FIG. 8] chromosomal translocation.

Expression of BAFF Receptors Variants

The specific conditions needed to propagate Bc-DLFL.1 raised the dependence of this lymphoma for tissue-derived factors for survival. The most likely candidates are the different receptors for BAFF. Exploiting the co-expression of MAC-1 and B220 by the lymphoma cells, thus separating them from the MAC-1 negative normal B cells we found that Bc-DLFL.1 cells co-expressed all three receptors (BAFF-R, BCMA and TACI) with BAFF-R showing the most intense labeling, while normal B cells expressed only BAFF-R at detectable levels [FIG. 12]. In normal B-cell development, TACI and BCMA is expressed following activation during plasmacytic differentiation, while BAFF-R disappears. BAFF-R is more characteristic of mature resting B-cells. Addition of recombinant BAFF moderately increased the short-term in vitro survival of Bc-DLFL.1 cells (not shown).

Immunoglobulin Gene Expression and Production in the Bc-DLFL.1 Lymphoma

Figure 4A:
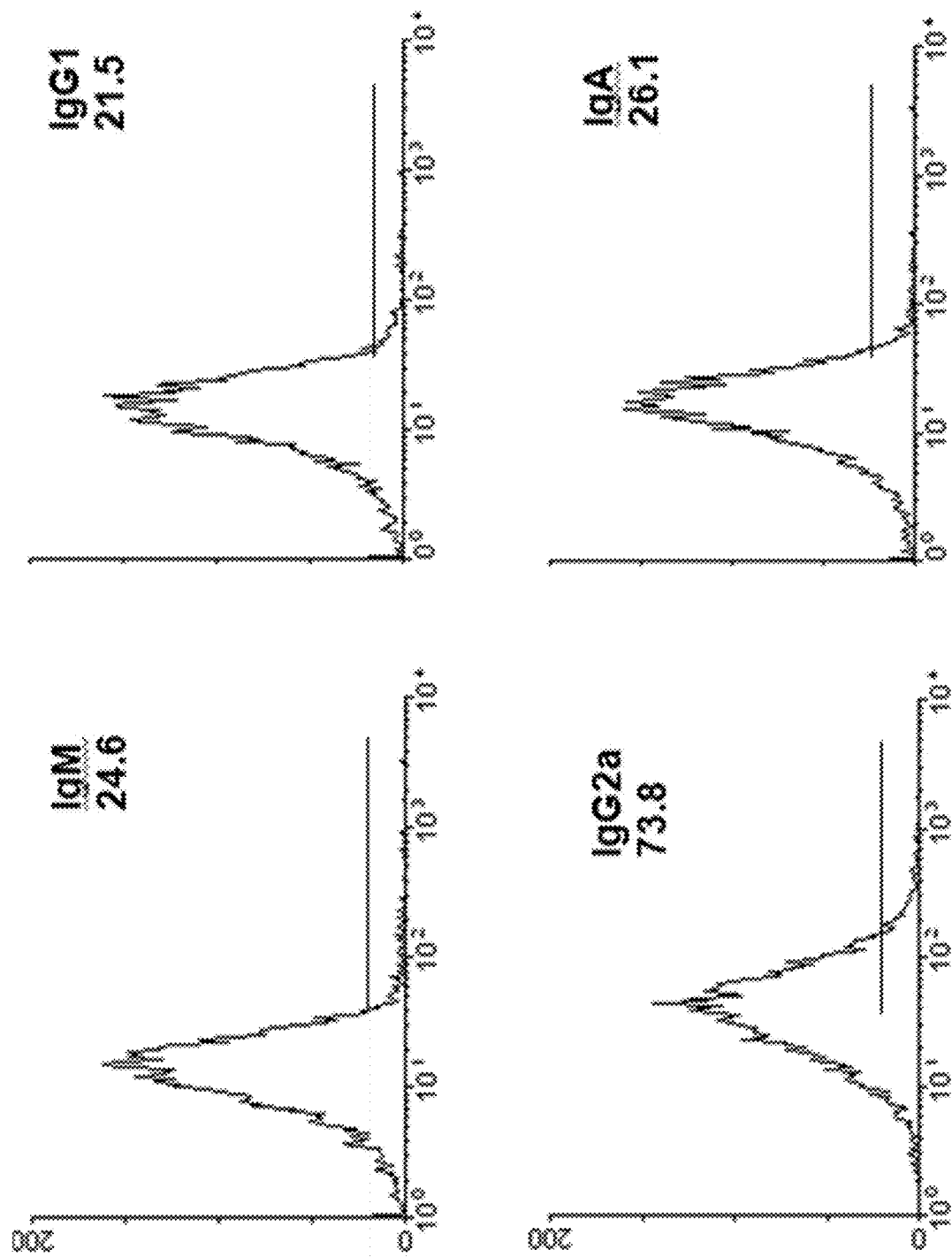

Most B-cell lymphomas in both humans and mice express productively rearranged immunoglobulin genes. To test whether such a rearrangement results in detectable cell surface immunoglobulin, we stained the lymphoma cells for IgM, IgD, IgG subclasses and IgA, in addition to kappa light chain. We found positive reactivity for kappa chain and IgG2a without the appearance of IgM, IgD, other IgG classes or IgA (FIG. 4a).

Flow cytometric analyses established that the lymphoma cells express MAC-1, CD19, MHC Class II, B220, supporting that the malignant transformation affected B cells. Furthermore, the expression of surface BcR of IgG2a/κ light chain isotype also indicates mature B-cell origin, unlike the frequent B-cell progenitor tumors observed in mice with conditional Pax5-deletion [12]. The combined phenotypic characterization and IgH V-region rearrangement analysis revealed that, within the B-lineage, the lymphoma cells most likely have originated from a germinal center stage subset, although its Bcl-6 protein expression is below the normal germinal center intensity, rendering this cell unclassifiable between germinal center (GCB) or activated B cell (ABC) regarding cell of origin.

Figure 4B:
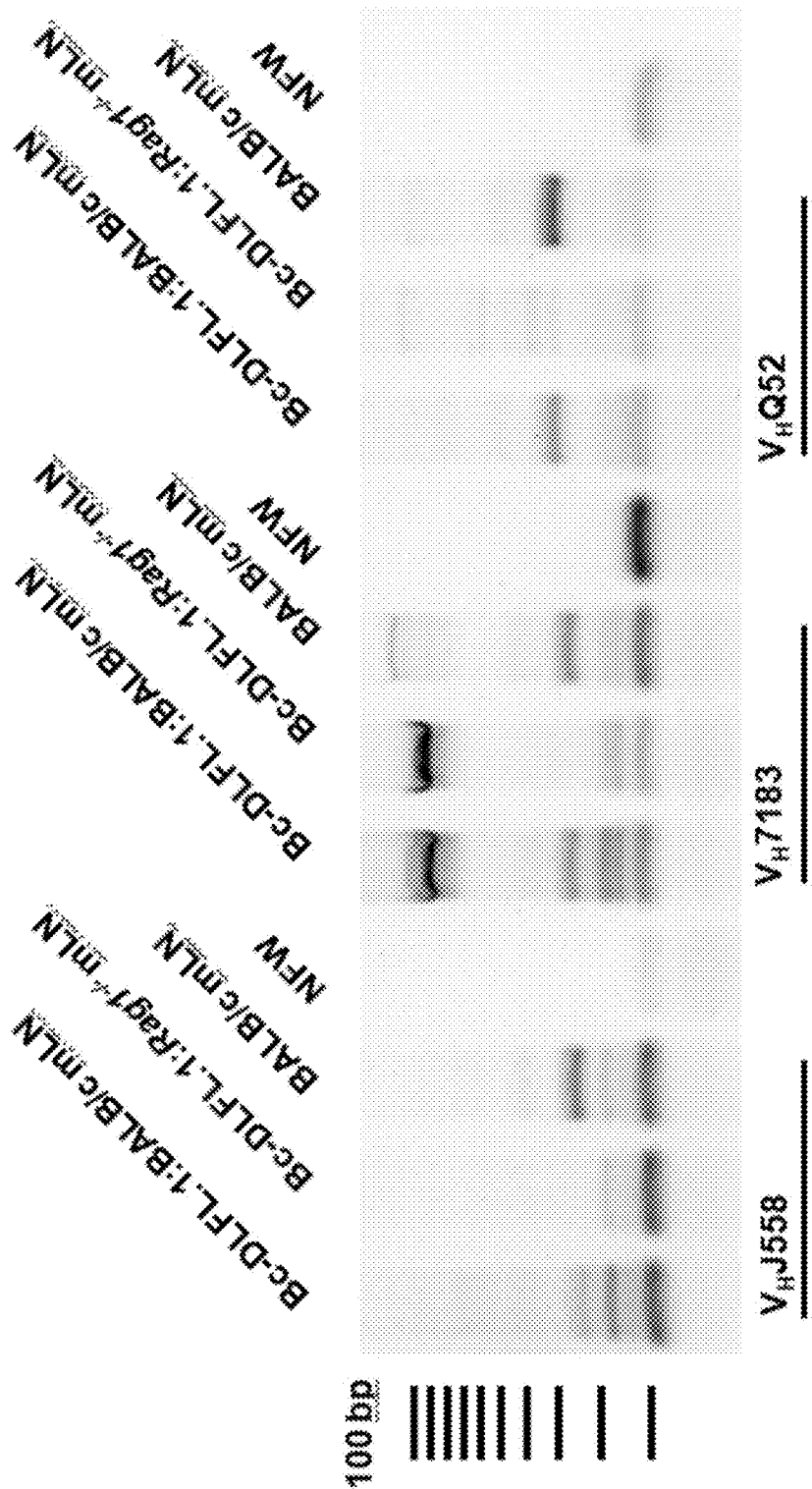

To determine the rearrangement pattern of the Ig heavy chain gene variable region of the Bc-DLFL.1 lymphoma we amplified the genomic DNA using VH-family specific primer pairs. We found rearrangement of IgH genes within the VH7183 region in lymphoma cells isolated from both BALB/c and Rag1−/− recipients using normal BALB/c mLN as reference sample for successful IgH V-region amplification (FIG. 4b). The analysis of IgH V-region rearrangement in both BALB/c and Rag2$^{-/-}$ recipients demonstrated identical IgH recombination involving the $V_H7183$ family only, despite the extensive interspersion with $V_HQ52$ family segments [16]. Rearrangement of IgH genes within the $V_H7183$ region in lymphoma cells isolated from both BALB/c and Rag1$^{-/-}$ recipients using normal BALB/c mLN as reference sample for successful IgH V-region amplification was also confirmed (FIG. 4b).

The presence of IgG2a/κ surface immunoglobulin indicated isotype switch, usually associated with B cells having undergone germinal center (GC) reaction coupled with Ig affinity maturation, in which process Bcl-6 transcriptional repressor plays a crucial role [14, 15]. As GC-derived B-cell lymphomas in humans overwhelmingly express of Bcl-6, next we investigated the presence of Bcl-6 in Bc-DLFL.1 by flow cytometry. Early studies found Bcl-6 expression in lymphoma cells. However, a later study using indirect immunohistochemistry using 4B2 anti-mouse Bcl6 and 15C anti-Bcl7A monoclonal antibodies on formaldehyde-fixed and paraffin-embedded tissue sections from mesenteric lymph nodes and spleen from control and lymphoma-bearing mice found no detectable Bcl6 expression at a level displayed by normal splenic centroblasts. On the other hand, while normal germinal center cells and follicles are devoid of Bcl7A labeling, we found a readily detectable expression both by marginal zone B cells and Bc-DLFL.1 cells. [FIG. 7] These results suggest that Bc-DLFL.1 is not directly originated from the germinal centers, or it represents a murine example for unclassifiable DLBCL type lymphomas, although post-germinal center location (i.e. marginal zone) origin is also likely.

Mesenterial Accumulation of Bc-DLFL.1 Cells

We found that fluorescence-labeled lymphoma cells rapidly accumulate in the mesenterium in the perivascular fat tissue, forming small lymphoma clusters arranged in a discrete bead-like pattern. Both in vivo bioimaging of lipophilic DiR dye-labeled lymphoma cells or CFSE-loaded cells detected by anti-fluorescein immunohistochemistry revealed identical pattern as condensed patches along the mesenterial fat, thus excluding labeling artifacts. The omental fat pads also showed an extensive accumulation of lymphoma cells, in agreement with previous reports on the involvement of this structure in the peritoneal homing of lymphocytes [FIG. 10]. Confocal microscopy investigations revealed that the docking sites for lymphoma cells are enriched for fibronectin, and form funnel-like structures on the perivascular fat pads, with LYVE-1-positive cells (possibly macrophages) scattered at the edge of such clusters [FIGS. 10 and 11].

Tissue Location of Bc-DLFL.1 Cells Independent from CXCR5

The lack of Bcl6 and the presence of Bcl7A raised that the propagation of the high-grade B-cell lymphoma cells occurs outside follicular location, thus bypassing the need for the recognition of CXCL13 chemokine by its cognate receptor CXCR5. Labeling of mesenteric lymph node from tumor-bearing mice revealed that while the residual small-sized lymphocytes preserve their CXCR5 display, the blast-sized B220-positive lymphoma cells are mostly negative or only weakly positive for this chemokine receptor [FIG. 9].

Preferential Expansion of Bc-DLFL.1 Cells in the Mesenterium and Mesenteric Lymph Nodes To monitor which organs can provide suitable microenvironment for the expansion of Bc-DLFL.1 cells we compared frequency of MAC-1/B220 double positive cells in the total lymphocyte population in various lymphoid organs, and calculated the fold increase as a measure of expansion. We found that the Day 7:Day 3 ratio was highest in the mesenteric lymph nodes and mesenterium (17× and 15.6×, respectively) followed by the spleen (5.9×) and least in the peripheral lymph nodes (4.4×) [FIG. 13].

Analysis of Homing Receptor Expression in Bc-DLFL.1 Lymphoma

Efficient homing to peripheral lymphoid tissues is initiated by specific interaction between recirculating leukocytes and endothelial cell surface adhesion molecules. We labeled freshly removed lymphoma cell suspension from mLN of Rag1$^{-/-}$ recipients with rat mAbs against LFA-1 (CD11α/CD18), ICAM-1 (CD54), L-selectin (CD62L) and α4 integrin. Bc-DLFL.1 lymphoma cells express ICAM-1 (CD54), L-selectin (CD62L) and α4 integrin. Expression of ICAM-1 and LFA-1 molecules is higher than that of L-selectin and α4 integrin (FIG. 5). This finding is in line with the specific spreading of the lymphoma cells in vivo, showing rapid colonization of the omentum and the FALC located along the blood vessels in the mesentery, a robust early enlargement of the mesenteric lymph nodes (mLN) over the largely preserved size and structure of peripheral lymph nodes (pLN). Bc-DLFL.1 lymphoma cells express very little or no CXCR5 chemokine receptor for the B-cell homeostatic CXCL13 chemokine produced by FDCs.

The combined level of ICAM-1 and LFA-1 seems sufficient to promote mLN-directed migration, as the high endothelial venules in mLN co-express PNAd and MAdCAM-1 addressins as docking molecules for L-selectin and α4 integrin, respectively, whereas the lower level of L-selectin reduces the degree of lymphoma homing to pLN where only PNAd acts as homing addressin [20].

Metastasis of Bc-DLFL.1 Lymphoma Cells to Mesenteric Lymph Nodes Involves Afferent Lymphatic Vessels of the Mesentery In addition to the enlarged spleen and mLN in lymphoma-bearing mice, we also noticed a substantial swelling of perivascular adipose cuffs surrounding the arterioles in the mesentery, a bi-layered sheet of mesothelium. HE staining combined with immunohistochemical labeling for B220 revealed that lymphoma cells accumulate both in the reticular perivascular connective tissue and in tight compact clusters in luminal arrangement (FIG. 6a/b/c). This latter arrangement of lymphoma cells in thin-walled dilated lumens raised that lymphatic vessels connecting the intestines and mesenteric lymph nodes could be involved in the expansion of tumor. To confirm the lymphatic identity of these vessels tissue sections from mesentery and mesenteric lymph nodes were reacted with anti-LYVE-1 mAb against lymphatic endothelium and also against VEGF-R2/flk-1 as blood endothelium marker or PNAd as high endothelial cell marker, respectively, in combination with anti-B220 labeling. We found that B220-positive cells were tightly packed within LYVE-1 positive lymphatic vessels in both the mesentery and in the entire lymphatic vasculature of the mesenteric lymph node. In contrast, the blood vasculature (including the PNAd-positive high endothelial venules) of mLNs only rarely contained B220-positive lymphoblasts [FIG. 6 d/e/f]. From these observations we conclude that the primary dissemination pathway of Bc-DLFL.1 cells from the abdominal cavity towards the mLNs involves the lymphatic vessels connecting the intestines and mLNs.

REFERENCES

[1] Deshpande A J, Buske C, Quintanilla-Martinez L and Fend F (2010) Molecular oncogenesis in Molecular pathology of hematolymphoid diseases Ed. Dunphy C H. Springer New York Dordrecht Heidelberg London pp. 3-21
[2] Morse H C 3rd, Anver M R, Fredrickson T N, Haines D C, Harris A W, Harris N L, Jaffe E S, Kogan S C, MacLennan I C, Pattengale P K, Ward J M (2002) Hematopathology subcommittee of the Mouse Models of Human Cancers Consortium. Bethesda proposals for classification of lymphoid neoplasms in mice. Blood. 100: 246-58.
[3] Donnou S, Galand C, Touitou V, Sautès-Fridman C, Fabry Z, Fisson S. Murine models of B-cell lymphomas: promising tools for designing cancer therapies. Adv Hematol. 2012; 2012:701704. doi: 10.1155/2012/701704.
[4] Kovalchuk A L, Qi C F, Torrey T A, Taddesse-Heath L, Feigenbaum L, Park S S, Gerbitz A, Klobeck G, Hoertnagel K, Polack A, Bornkamm G W, Janz S, Morse H C 3rd. (2000) Burkitt lymphoma in the mouse. J Exp Med. 192:1183-90.

[5] Strasser A, Harris A W, Vaux D L, Webb E, Bath M L, Adams J M, Cory S. (1990) Abnormalities of the immune system induced by dysregulated bcl-2 expression in transgenic mice. Curr Top Microbiol Immunol.; 166:175-81.

[6] Egle A, Harris A W, Bath M L, O'Reilly L, Cory S. (2004) VavP-Bcl2 transgenic mice develop follicular lymphoma preceded by germinal center hyperplasia. Blood. 103:2276-83.

[7] Balogh P. and Lábadi P. (2011) Structural Evolution of the Spleen in Man and Mouse in Developmental Biology of Peripheral Lymphoid Organs Ed. P. Balogh Springer-Verlag Berlin Heidelberg 2011, pp. 121-142

[8] Kim H J, Kammertoens T, Janke M, Schmetzer O, Qin Z, Berek C, Blankenstein T. (2004) Establishment of early lymphoid organ infrastructure in transplanted tumors mediated by local production of lymphotoxin alpha and in the combined absence of functional B and T cells. J Immunol. 172:4037-47.

[9] Höpken U E, Rehm A. (2012) Homeostatic chemokines guide lymphoma cells to tumor growth-promoting niches within secondary lymphoid organs. J Mol Med (Berl). 90:1237-45.

[10] Mombaerts, P., J. Iacomini, R. S. Johnson, K. Herrup, S. Tonegawa, and V. E. Papaioannou. (1992) RAG-1-deficient mice have no mature B and T lymphocytes. Cell. 68: 869-877.

[12] Cobaleda C, Jochum W, Busslinger M. (2007) Conversion of mature B cells into T cells by dedifferentiation to uncommitted progenitors. Nature. 449:473-7.

[13] Frith C G and Wiley L D (1981). Morphologic classification and correlation of incidence of hyperplastic and neoplastic hematopoietic lesions in mice with age. J Gerontol 36:534-545.

[14] Bunting K L, Melnick A M. (2013) New effector functions and regulatory mechanisms of BCL6 in normal and malignant lymphocytes. Curr Opin Immunol. 25:339-46.

[15] Basso K, Dalla-Favera R. (2012) Roles of BCL6 in normal and transformed germinal center B cells Immunol Rev. 247: 172-83.

[16] Johnston C M, Wood A L, Bolland D J, Corcoran A E. (2006) Complete sequence assembly and characterization of the C57BL/6 mouse Ig heavy chain V region. J Immunol. 176:4221-34.

[17] Fu Y X, Huang G, Wang Y, Chaplin D D. (1998) B lymphocytes induce the formation of follicular dendritic cell clusters in a lymphotoxin alpha-dependent fashion. J Exp Med. 187:1009-18.

[18] Donnou et al MurineModels of B-Cell Lymphomas: Promising Tools for Designing Cancer Therapies Advances in Hematology Volume 2012, Article ID 701704

[19] Morse et al Bethesda proposals for classification of lymphoid neoplasms in mice Blood, 1 Jul. 2002 Volume 100, Number 1 246-258

[20] Rosen S D. (2004) Ligands for L-selectin: homing, inflammation, and beyond. Annu Rev Immunol.; 22:129-56.

[21] Donnou et al MurineModels of B-Cell Lymphomas: Promising Tools for Designing Cancer Therapies Advances in Hematology Volume 2012, Article ID 701704

[22] Rosenthal A, Younes A. High grade B-cell lymphoma with rearrangements of MYC and BCL2 and/or BCL6: Double hit and triple hit lymphomas and double expressing lymphoma. Blood Rev. 2016 Sep. 30. pii: S0268-960X(16)30048-0. doi:10.1016/j.blre.2016.09.004.

[23] S. Mori, R. E. Rempel, J. T. Chang et al., "Utilization of pathway signatures to reveal distinct types of B lymphoma in the Eµ-myc model and human diffuse large B-cell lymphoma," *Cancer Research*, vol. 68, no. 20, pp. 8525-8534, 2008.

[24] Gashev A A. (2010) Basic mechanisms controlling lymph transport in the mesenteric lymphatic net. Ann N Y Acad Sci. 1207 Suppl 1:E16-20.

[25] Koganei et al B-1a cell origin of the murine B lymphoma line BCL1 characterized by surface markers and bacterial reactivity of its surface IgM. Immunol Lett. 2005 May 15; 98(2):232-44.)

[26] Borrello et al Fibroblast-Secreted Macrophage Colony-Stimulating Factor Is Responsible for Generation of Biphenotypic B/Macrophage Cells from a Subset of Mouse B Lymphocytes. The Journal of Immunology Oct. 1, 1999 vol. 163 no. 7 3605-3611.

[27] Gu and Rajewsky B cell Protocols, Methods in Molecular Biology, Vol 271, 2004

[28] Buchwalow, Igor B., Böcker, Werner Immunohistochemistry: Basics and Methods; Renshaw: Immunohistochemistry—Methods Express Book Series

The invention claimed is:

1. A method for assessment of an effect of an agent on lymphoma cells, said method comprising
administering to a mouse
lymphoma cells, said lymphoma cells being of the mouse lymphoma cell line deposited at the Deutsche Sammlung von Mikroorganismen und Zellkulturen (DSMZ) on Sep. 24, 2015 under the number DSMZ ACC3278 or derived therefrom, wherein said lymphoma cells are positive for CD19, B220, MHC II, surface IgG2a/kappa chain and MAC-1, and negative for CD5, and
an agent of interest, and
evaluating the effect of the agent on the propagation or migration of the lymphoma cells.

2. The method according to claim 1 wherein said lymphoma cells comprise a chromosomal translocation selected from the group consisting of the following translocations: t(10:6), t(6:10), t(11:19) and t(10:11).

3. The method according to claim 1, wherein said lymphoma cells, when administered intraperitoneally to the mouse in a dose of $10^4$ to $5 \times 10^6$ cells/recipient, expand to one or more site(s) selected from the omentum and the fat associated lymphoid clusters (FALC) along the blood vessels in the mesentery within 7 days after the administration.

4. The method according to claim 3, wherein said lymphoma cells, upon said administration, expand to said expansion site(s) within 5 days after the administration.

5. The method according to claim 1, wherein said lymphoma cells, when administered intraperitoneally to the mouse in a dose of $10^4$ to $5 \times 10^6$ cells/recipient, are substantially absent from a tissue or organ selected from: spleen, peripheral lymph nodes and liver up to 8 days after the administration.

6. The method according to claim 5, wherein the lymphoma cells are substantially absent from a tissue or organ selected from: spleen, peripheral lymph nodes and liver up to 3 days after the administration.

7. The method according to claim 1, wherein said lymphoma cells, when administered intraperitoneally to the mouse the mouse in a dose of $10^4$ to $5 \times 10^6$ cells/recipient, are absent from a tissue or organ selected from: bone marrow, thymus, brain, kidney, muscle, Peyer's patches and lung up to 8 days after the administration.

8. The method according to claim 1, wherein the lymphoma cells, when administered intraperitoneally to the mouse in a dose of $10^6$ to $5\times10^6$ cells/recipient, expand to one or more site(s) selected from the omentum and the fat associated lymphoid clusters (FALC) along the blood vessels in the mesentery within 3 days after the administration.

9. The method according to claim 1, wherein the lymphoma cells, when administered intraperitoneally to the mouse in a dose of $10^6$ to $5\times10^6$ cells/recipient, are substantially absent from a tissue or organ selected from: spleen, peripheral lymph nodes and liver up to 5 days after the administration.

10. The method according to claim 1, wherein said lymphoma cells, when administered intraperitoneally to the mouse in a dose of $10^4$ to $5\times10^6$ cells/recipient, are absent from a tissue or organ selected from: bone marrow, thymus, brain, kidney, muscle, Peyer's patches and lung up to 12 days after the administration.

11. The method according to claim 1, wherein said lymphoma cells, when administered intraperitoneally to the mouse in a dose of $10^6$ to $5\times10^6$ cells/recipient, are absent from a tissue or organ selected from: bone marrow, thymus, brain, kidney, muscle, Peyer's patches and lung up to 8 days after the administration.

12. The method according to claim 1, wherein the lymphoma cells, when administered intraperitoneally to the mouse in a dose of $10^4$ to $5\times10^6$ cells/recipient, expand to abdominal lymphatic tissue showing adhesion to the lymphoma cells mediated by PNAd and MAdCAM within 7 days from the administration.

13. The method according to claim 12, wherein the lymphoma cells, when administered intraperitoneally to the mouse in a dose of $10^4$ to $5\times10^6$ cells/recipient, expand to abdominal lymphatic tissue showing adhesion to the lymphoma cells mediated by PNAd and MAdCAM within 2 days from the administration.

14. The method according to claim 12, wherein the lymphoma cells, when administered intraperitoneally to the mouse in a dose of $10^6$ to $5\times10^6$ cells/recipient, expand to abdominal lymphatic tissue showing adhesion to the lymphoma cells mediated by PNAd and MAdCAM within 5 days from the administration.

15. A method for assessment of B-cell lymphoma expansion, the method comprising
administering lymphoma cells to a mouse intraperitoneally in a dose of $10^4$ to $5\times10^6$ cells/recipient, said lymphoma cells being of the mouse lymphoma cell line deposited at the Deutsche Sammlung von Mikroorganismen und Zellkulturen (DSMZ) on Sep. 24, 2015 under the accession number DSMZ ACC3278 or derived therefrom, wherein the lymphoma cells are positive for CD19, B220, MHC II, surface IgG2a/kappa chain and MAC-1, and negative for CD5, and
detecting the localization of the lymphoma cells, which are positive for CD19, B220, MHC II, surface IgG2a/kappa chain and MAC-1 and negative for CD5.

16. The method according to claim 15, wherein the lymphoma cells comprise a chromosomal translocation selected from the group consisting of the following translocations: t(10:6), t(6:10), t(11:19) and t(10:11).

17. The method according to claim 15, wherein the lymphoma cells are administered in a dose of $10^6$ to $5\times10^6$ cells/recipient.

18. The method according to claim 15, wherein the detection is performed within 7 days after the administration.

19. The method according to claim 15, wherein the detection is performed within 5 days after the administration.

20. The method according to claim 15, wherein the lymphoma cells are detected in tissues showing adhesion mediated by PNAd and MAdCAM.

21. The method according to claim 15, wherein the lymphoma cells are detected in the omentum and/or the fat associated lymphoid clusters (FALC) along the blood vessels in the mesentery.

22. An in vitro method for assessment of an effect of an agent on lymphoma cells or on interaction of lymphoma cells and tumor microenvironment, said method comprising
providing lymphoma cells, said lymphoma cells being of the cell line deposited at the Deutsche Sammlung von Mikroorganismen and Zellkulturen (DSMZ) on Sep. 24, 2015 under the accession number DSMZ ACC3278 or derived therefrom, wherein said lymphoma cells are positive for CD19, B220, MHC II, surface IgG2a/kappa chain and MAC-1, and negative for CD5,
culturing the lymphoma cells in the presence and/or absence of tumor stroma,
administering the agent to the culture,
evaluating, optionally while considering the presence and/or absence of tumor stroma, the effect of the agent on the propagation of the lymphoma cells.

23. The in vitro method according to claim 22, wherein the lymphoma cells comprise a chromosomal translocation selected from the group consisting of the following translocations: t(10:6), t(6:10), t(11:19) and t(10:11).

24. A method for propagation of a population of lymphoma cells, said lymphoma cells being of the cell line deposited at the Deutsche Sammlung von Mikroorganismen and Zellkulturen (DSMZ) on Sep. 24, 2015 under accession number DSMZ ACC3278 or derived therefrom, wherein said lymphoma cells are positive for CD19, B220, MHC II, surface IgG2a/kappa chain and MAC-1, and negative for CD5, comprising
injecting the lymphoma cells into a recipient mouse,
obtaining further lymphoma cells positive for CD19, B220, MHC II, surface IgG2a/kappa, and MAC-1, and negative for CD5 and tumor stroma from the mouse,
co-culturing the further lymphoma cells positive for CD19, B220, MHC II, surface IgG2a/kappa, and MAC-1, and negative for CD5 and the tumor stroma obtained from the mouse in a culture medium suitable for B-lineage cells.

* * * * *